United States Patent [19]

Levy

[11] Patent Number: 5,589,470
[45] Date of Patent: Dec. 31, 1996

[54] REDUCING TETRACYCLINE RESISTANCE IN LIVING CELLS

[75] Inventor: Stuart B. Levy, Boston, Mass.

[73] Assignee: Trustees of Tufts College, Medford, Mass.

[21] Appl. No.: 232,247

[22] PCT Filed: Oct. 16, 1992

[86] PCT No.: PCT/US92/08965

§ 371 Date: Jun. 14, 1994

§ 102(e) Date: Jun. 14, 1994

[87] PCT Pub. No.: WO93/08806

PCT Pub. Date: May 13, 1993

Related U.S. Application Data

[63] Continuation-in-part of Ser. No. 788,693, Nov. 6, 1991, abandoned, which is a continuation of Ser. No. 672,323, Mar. 20, 1991, Pat. No. 5,258,372, and Ser. No. 484,904, Feb. 26, 1990, Pat. No. 5,064,821.

[51] Int. Cl.$^6$ .................................................. A61K 31/65
[52] U.S. Cl. ................................................................ 514/154
[58] Field of Search ................................................... 514/154

[56] References Cited

U.S. PATENT DOCUMENTS

| | | | |
|---|---|---|---|
| 3,236,736 | 2/1966 | Fitch et al. | 514/154 |
| 3,454,697 | 7/1969 | Joyner et al. | 514/154 |
| 3,579,564 | 5/1971 | Blackwood et al. | 552/204 |
| 3,863,009 | 1/1975 | Johnston | 424/227 |
| 4,024,272 | 5/1977 | Rogalski et al. | 424/275 |
| 4,126,680 | 11/1978 | Armstrong | 424/80 |
| 4,806,529 | 2/1989 | Levy | 514/154 |
| 5,021,407 | 6/1991 | Levy | 514/154 |
| 5,064,821 | 11/1991 | Levy | 514/154 |
| 5,258,372 | 3/1991 | Levy | 514/154 |

FOREIGN PATENT DOCUMENTS

WO84/1895  5/1984  WIPO.

OTHER PUBLICATIONS

Grassi, et al., *New Trends in Antibiotics: Research & Therapy*, pp. 3–55 (1981).

Levy, S. B., "The Tetracyclines: Microbial Sensitivity and Resistance", *New Trends in Antibiotics: Research and Therapy*, Elsevier/North–Holland Biomedical Press, 1981, pp. 27–44.

Chopra et al., "The Tetracyclines: Prospects at the Beginning of the 1980's", *Journal of Microbial Chemotherapy*, 8:5–21 (1981).

Lehninger, *Biochemistry—The Molecular Basis of Cell Structure and Function* (2 ed., Worth Publishers, 1975) p. 941.

Mendez, B. et al., "Heterogeneith of Tetracycline Resistance Determinants," *Plasmid*, 3:99–108 (1980).

Levy and McMurry, "Detection of an Inducible Membrane Protein Associated with R–Factor Mediated Tetracycline Resistance," Biochemical and Biophysical Research Commun. 56(4):1060–1068 (1974).

Levy and McMurry, "Plasmid–Determined Tetracycline Resistance Involves New Transport Systems for Tetracycline," *Nature*, 275 (5683):90–92 (1978).

McMurry and Levy, "Two Transport Systems for Tetracycline in Sensitive *Escherichia coli*: Critical Role for an Initial Rapid Uptake System Insensitive to Energy Inhibitors", *Antimicrobial Agents and Chemotherapy* 14(2):201–209 (1978).

McMurry et al., "Active Efflux of Tetracycline Encoded by Four Genetically Different Tetracycline Resistant Determinants in *Escherichia coli*," *Proc. Nat. Acad. of Sci.*, U.S.A., 77(7):3974–3977 (1980).

Curiale and Levy, "Two Complementation Groups Mediate Tetracycline Resistance Determined by Tn10", *Journal of Bacteriology*, 151(1); 209–215 (1982).

Korolkovas, A. et al., *Essentials of Medicinal Chemistry* (John Wiley & Sons, Inc., 1976) at 512–517.

McMurry et al., "Active Uptake of Tetracycline by Membrane Vesicles from Susceptible *Escherichia coli*," *Antimicrobial Agents and Chemotherapy*, 20(3):307–313 (1981).

Brock et al., "Comparison of the In Vitro Serum Microbiological Activity of a Triple Tetracycline Tablet, 300 mg B.I.D. with Oxytetracycline, 250 mg Q.I.D.", *J. Int. Med. Res.* (1981), 9, 360–364.

Primary Examiner—Theodore J. Criares
Attorney, Agent, or Firm—David G. Conlin; Peter F. Corless

[57] ABSTRACT

The present invention provides an improved methodology by which therapeutically to overcome resistance to tetracycline in living cells including bacteria, parasites, fungi, and rickettsiae. The methodology employs a blocking agent such as C5 ester derivatives, or 13-(substituted mercapto) derivatives of tetracycline, in combination with other tetracycline-type antibiotics as a synergistic combination of compositions to be administered simultaneously, sequentially or concurrently. In another embodiment, C5 ester novel compositions are provided which may be administered alone against, for example, a sensitive or resistant strain of gram positive bacteria such as *S. aureus* and *E. faecalis*. The concomitantly administered compositions effectively overcome the tetracycline resistant mechanisms present such that the cell is effectively converted from a tetracycline-resistant state to a tetracycline-sensitive state.

27 Claims, No Drawings

REDUCING TETRACYCLINE RESISTANCE IN LIVING CELLS

This is a continuation of International Application PCT/US92/08965, with an international filing date of Oct. 16, 1992, now abandoned, and which is a continuation-in-part of U.S. application Ser. No. 07/788,693, filed Nov. 6, 1991, now abandoned, and which is a continuation of U.S. application Ser. No. 07/672,323, filed Mar. 20, 1991, now issued as U.S. Pat. No. 5,258,372 and U.S. application Ser. No. 07/484,904, filed Feb. 26, 1990, now issued as U.S. Pat. No. 5,064,821.

RESEARCH REPORT

The research for the present invention was supported by funds obtained through Tufts University.

1. Field of the Invention

The present invention concerns therapeutic tetracycline treatment of living cells, and is particularly directed to methods and materials for altering and overcoming resistance to tetracycline within microorganisms such as bacteria, fungi, rickettsia, and the like.

2. Background of the Invention

The development of the tetracycline antibiotics was the direct result of a systematic screening of soil specimens collected from many parts of the world for evidence of microorganisms capable of producing bacteriocidal and/or bacteriostatic compositions. The first of these novel compounds was introduced in 1948 under the name chlortetracycline. Two years later oxytetracycline became available. The detailed elucidation of the chemical structure of these agents confirmed their similarity and furnished the analytical basis for the production of a third member of this group in 1952, tetracycline. By 1957, a new family of tetracycline compositions characterized chemically by the absence of the ring-attached $CH_3$ group present in the earlier compositions was prepared and became publicly available in 1959 under the official name demeclocycline. Subsequently, methacycline, a derivative of oxytetracycline, was introduced in 1966; doxycycline became available by 1967; and minocycline was in use by 1972. For clarity, for general ease of understanding, and for comparison purposes, these individual tetracycline type agents are structurally compared within Table I below.

TABLE I

TETRACYCLINE

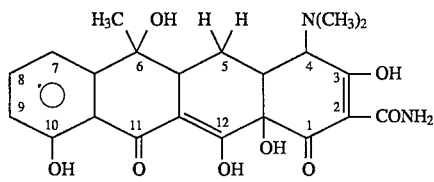

| Congener | Substituent(s) | At Carbon Position Nos. |
|---|---|---|
| Chlortetracycline | —Cl | (7) |
| Oxytetracycline | —OH, —H | (5) |
| Demeclocycline | —OH, —H; —Cl | (6; 7) |
| Methacycline | —OH, —H; =$CH_2$ | (5; 6) |
| Doxycycline | —OH, —H; —$CH_3$, —H | (5; 6) |
| Minocycline | —H, —H; —N($CH_3$)$_2$ | (6; 7) |

Subsequent to these initial developments, much research effort was focused on developing new-tetracycline antibiotic compositions effective under varying therapeutic conditions and routes of administration; and for developing new tetracycline analogues which might prove to be equal or more effective than the originally introduced tetracycline families beginning in 1948. Representative of such developments are U.S. Pat. Nos. 3,957,980; 3,674,859; 2,980,584; 2,990,331; 3,062,717; 3,557,280; 4,018,889; 4,024,272; 4,126,680; 3,454,697; and 3,165,531. It will be understood that these issued patents are merely representative of the range of diversity of investigations seeking tetracycline and tetracycline analogue compositions which are pharmacologically active.

Historically, soon after their initial development and introduction, the tetracyclines regardless of specific formulation or chemical structure were found to be highly effective pharmacologically against rickettsiae; a number of gram-positive and gram-negative bacteria; and the agents responsible for lymphogranuloma venereum, inclusion conjunctivitis, and psittacosis. Hence, tetracyclines became known as "broad spectrum" antibiotics. With the subsequent establishment of their in-vitro antimicrobial activity, effectiveness in experimental infections, and pharmacological properties, the tetracyclines as a class rapidly became widely used for therapeutic purposes. However, this widespread use of tetracyclines for both major and minor illnesses and diseases led directly to the emergence of resistance to these antibiotics even among highly susceptible bacterial species both commensal and pathogenic—as for example pneumococci and *Salmonella*. The rise of tetracycline-resistant organisms has led not only to a general decline in use of tetracyclines and tetracycline analogue compositions as antibiotics of choice, but has also launched major efforts and investigations to uncover the mechanism for tetracycline resistance— in the hope that some effective means might be developed to overcome the problem of tetracycline-resistance and thus reestablish the pharmacological value and efficacy of tetracyclines as a whole.

The following represents a current summary of the investigations and knowledge regarding the mechanism of action for tetracyclines in bacteria. The principal site of action for tetracyclines is the bacterial ribosome; at least two different processes appear to be required for tetracyclines to gain access to the cytoplasm and the ribosomes of bacteria. The first process is a passive diffusion of the tetracycline through hydrophilic pores located in the outer cell membrane. One of these structures is the major outer membrane protein, Omp F in *E. coli*. The second process involves an energy-dependent active transport system that pumps all tetracyclines through the inner cytoplasmic membrane into the cytoplasm of the cell. In the tetracycline-sensitive cell or organism, once the tetracycline gains access to the interior of the cell, it is able to bind to the ribosomes and inhibit protein synthesis. However, in many tetracycline resistant cells and organisms, an efflux pump system is present which appears to bind the tetracycline molecule and actively transports the tetracycline molecule out of the organism into the surrounding environment. This active efflux employs an inner membrane protein designated TET (or Tet) protein which is synthesized in the cell from a gene which is generally acquired by the organism. Often the gene is present on an extra-chromosomal, autonomously replicating plasmid or a transposon.

Tetracycline resistance is often regulated—that is, inducible by tetracycline. Investigations of active tetracycline efflux systems and the details of the active efflux mechanism of action have been well documented and include the following publications, each of which is expressly incorporated by reference herein: Chopra et al., *J. Antimicrobiol. Chemotherapy* 8:5–21 (1981); Levy and McMurry, *Biochem. Biophys. Res. Comm.* 56:1060–1068 (1974); Levy and McMurry, *Nature* 275:90–92 (1978); McMurry and Levy, *Antimicrobial Agents And Chemotherapy* 114:201–209 (1978); McMurry et al., *Proc. Nat. Acad. Sci. U.S.A.* 77:3974–3977 (1980); Ball et al., *Biochem. Biophys. Res. Comm.* 93:74–81 (1980); Curiale and Levy, *J. Bact.* 151:209–2115 (1982); Mendez et al., *Plasmid* 3:99–108 (1980); Curiale et al., *J. Bact.* 157:211–217 (1984); and Levy, S. B., *Journal of Antimicrobial Chemotherapy* 24:1–3 (1989).

In addition, a second mechanism of tetracycline resistance for cells is known and in effect. This resistance mechanism involves a cytoplasmic protein which protects the intracellular ribosomes from the inhibitory action of tetracyclines. This form of tetracycline resistance is described within Burdett, V., *J. Bact.* 165:564–569 (1986); and Levy, S. B., *J. Antimicrob. Chem.* 24:1–3 (1989).

With the increased understanding and knowledge regarding the origin and the mechanisms of tetracycline resistance in various cells and microorganisms, active investigations and developments seeking means for overcoming these mechanisms, notably the active efflux system have been attempted. One successful approach is described within U.S. Pat. No. 4,806,529 issued Feb. 21, 1989—an innovation which is a precursor of more recent developments, namely U.S. Pat. No. 5,064,821 issued Nov. 12, 1991. Clearly, additional methods and materials for overcoming tetracycline-resistance in bacteria and other organisms are most desirable and needed. Substantive advances which additionally overcome the active efflux system for tetracycline and/or the ribosomal protection mechanism in the resistant cell would be presently recognized by the ordinary practitioner in the art as a major asset and innovation.

SUMMARY OF THE INVENTION

The present invention provides methods and compositions for therapeutically treating a tetracycline-resistant cell and also provides a method for altering a cell from a tetracycline-resistant state into a tetracycline-sensitive state. In one preferred embodiment, this method comprises the steps of: administering to the cell a predetermined quantity of at least a first composition selected from the chemical group consisting of a blocking agent which is capable of interacting with, e.g. binding to, a product of at least one tetracycline resistance determinant capable of protecting ribosomes in the cell from tetracycline's inhibitory activity; and concomitantly administering to the cell a pre-determined quantity of at least a second composition selected from the chemical group consisting of tetracycline, tetracycline analogues, and tetracycline derivatives which are not said blocking agent. The cell is allowed to preferentially react with the blocking agent.

The unique methodology is able to alter and to convert tetracycline-resistant cells or microorganisms into tetracycline-sensitive ones; and, accordingly, to provide a therapeutic treatment for those living subjects, human, animal, and plants, which have been previously refractory to a tetracycline therapeutic regimen.

In another embodiment, certain novel compositions are provided which may be administered alone against, for example, a sensitive or resistant strain of gram positive bacteria such as *S. aureus* and *E. faecalis*.

DETAILED DESCRIPTION OF THE PREFERRED EMBODIMENTS

The present invention represents a unique methodology by which to overcome the increasing resistance of many different varieties of cells and microorganisms to the antibiotic activity of tetracyclines, their analogues and derivatives. The present invention takes into account and acts upon the existence of specific DNA sequences, which are typically found on plasmids and transposons, and which specify proteins for tetracycline-resistance determinants. Some of these determinants act via an active efflux system which maintains an intracellular tetracycline concentration below those levels able to inhibit protein synthesis within the microorganism such as described in above-mentioned U.S. Pat. No. 4,806,529. Other determinants act by protecting the ribosome from tetracycline's inhibitory activity, e.g. by binding with tetracycline. The present invention represents improvement in efficacious and reliable techniques for overcoming tetracycline resistance in living cells and thus for reestablishing tetracyclines as an antibiotic of choice in the treatment of infectious diseases caused by the ever-increasing variety and diversity of disease agents. The invention relies on the action of a blocking agent which is capable of interacting with a product of at least one tetracycline resistance determinant which acts by protecting the cell from tetracycline's inhibitory activity. The determinant is capable of making a product, such as a cytoplasmic protein, which interacts with the ribosomes to make them tetracycline resistant or a membrane protein which keeps tetracycline out of the cell.

The present invention is intended for use with tetracycline-resistant cells or organisms which are found to contain or carry a product of the genetic determinants responsible for tetracycline resistance, and in particular, those which are due to protection of the ribosome from the inhibitory activity of tetracycline. As described within the recent publication of Levy, S. B., *Journal of Antimicrobial Chemotherapy* 24:1–3 (1989), the text of which is expressly incorporated by reference herein, more than a dozen different distinguishable tetracycline resistance determinants have been uncovered [Levy, S. B., "Resistance to the Tetracyclines," in *Antimicrobial Drug Resistance,* (Bryan, L. E., editor), Academic Press, Orlando, Fla., 1984, pages 191–204; Levy, S. B., *ASM News* 54:418–421 (1988)]. As these genetic determinants of these tetracycline-resistant cells have been elucidated, it has become generally accepted that the same or very similar genes are responsible for resistance in a large number of different aerobic and anaerobic microorganisms.

The present invention is therefore believed suitable for use with at least, but not exclusively, the following genera: Gram-negative genera, in particular *Enterobacteriaceae,* which harbor Class A–E tetracycline resistance determinants; Gram-positive genera including streptococci, staphylococci, and bacillus species which bear the Class K and L tetracycline resistance determinants; aerobic and anaerobic microorganisms bearing the Class M, O or Q determinants represented by *Streptococcus agalactiae, Bacteroides, Enterococcus, Gardnerella* and *Neisseria* species, Mycoplasma and Ureaplasma, and *Clostridium; Clostridium perfringens* bearing the Class P tetracycline-resistant determinant.

It will be recognized and appreciated that the above listed organisms are themselves only representative and illustrative of the range, variety, and diversity of cell types, bacterial species, fungi, parasites, and rickettsial disease agents which may be therapeutically treated using the present methodology. It will be expressly noted that no specific class, genus, species, or family of cell, microorganism, or parasite is excluded; to the contrary, it is expected that with future investigations into the determinants responsible for tetracycline resistance, ever greater numbers of different cells will be recognized as suitable for efficacious treatment using the present invention. In addition, in view of the recent use of tetracyclines for treatment of neoplasms, it is deemed that the present methodology would be useful in such therapies [van der Bozert et al., Cancer Res. 48:6686–6690 (1988)].

The present invention represents a major improvement over presently known methods for dealing with tetracycline resistance within disease-causing cells and organisms. In one preferred embodiment, the methodology requires only two essential steps: the administration to the tetracycline-resistant cell of a predetermined quantity of at least a first composition selected from the chemical group consisting of a blocking agent which is capable of interacting with a product of at least one tetracycline resistance determinant which is capable of protecting ribosomes in the cell from tetracycline's inhibitory activity; and concomitantly administering to the cell a pre-determined quantity of at least a second composition selected from the chemical group consisting of tetracycline, tetracycline analogues, and tetracycline derivatives which are not said blocking agent.

As noted above, in another embodiment, certain novel compositions are provided which may be administered alone against, for example, a sensitive or resistant strain of gram positive bacteria such as *S. aureus* and *E. faecalis*.

Examples of products of a tetracycline resistance determinant are Tet M, Tet O and Tet Q proteins for cytoplasmic protein products and Tet A, Tet B, Tet K and Tet L for membrane products.

The resistance mechanism of the cell is allowed to preferentially react with the blocking agent so avoiding preferential reaction with the second administered composition which is the tetracycline, a tetracycline analogue or derivative composition.

Clearly, therefore, it is recognized and understood that in this preferred embodiment two different compositions are to be administered concurrently, sequentially or simultaneously to the tetracycline-resistant cell. Moreover, it will be noted that the methodology requires and relies upon a preferential binding and reaction with the administered blocking agent in-situ; and consequently demonstrate a substantial lack of attraction or preference for the other administered tetracycline composition, analogue, or derivative present in-situ. The operation, utility, and efficacy of the present methodology is thus based upon an empirically demonstrable preference of the tetracycline-resistant cell for one class of composition over another when both classes of composition are introduced concomitantly—that is, concurrently, sequentially or simultaneously to the resistant cell.

To date, there is no basis, system, or technique which can be employed to accurately predict which of two similar tetracycline formulations and chemical structures would be preferentially reactive with the resistance systems of cells. Earlier investigations as described within U.S. Pat. No. 4,806,529 issued Feb. 21, 1989, have demonstrated that when tetracycline [i.e., 4-(Dimethylamino)-1,4,4a,5,5a,6-11,12a-octahydro-3,6,10,12,12a-pentahydroxy-6-methyl-1-11-dioxo-2-naphth acenecarboxamide] is administered concurrently or simultaneously with other tetracycline analogues and derivatives such as minocycline or thiatetracycline, it is not actively effluxed from the cell and consequently enters tetracycline-resistant cells. Further studies have demonstrated that 13-thiol derivatives of methacycline are able to block the efflux protein and inhibit the resistance mechanism in both gram negative and gram positive cells, including different mechanisms of resistance, namely efflux and ribosome protection (See U.S. Pat. No. 5,064,821). The present invention expands upon these earlier investigations in substantial degree. It also provides the user with novel blocking agents which unexpectedly have been found to show very high inhibition of the mechanisms for ribosome protection as well as efflux.

In one embodiment of the invention, the blocking agent is a tetracycline analogue which contains a sufficient part of tetracycline to interact with a product of at least one tetracycline resistance determinant capable of protecting cells from tetracycline's inhibitory activity.

One specific class of blocking agents is the class of 13-(substituted mercapto) tetracyclines of the formula (Formula I):

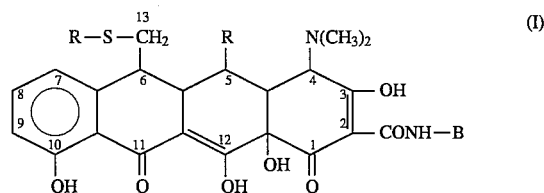

wherein

A is selected from the group consisting of hydrogen and a hydroxyl group;

B is selected from the group consisting of a hydrogen atom, a methylene group, and any linear, branched, or ring structure comprising from 1–6 carbon atoms and optionally including heteroatoms such as oxygen and nitrogen atoms; and R is selected from the group consisting of organic entities comprising from 1–12 carbon atoms, with or without other heteroatoms including sulfur, oxygen, halogen, nitrogen, and the like, and takes form as linear, branched, or cyclic alkyl, aryl, or alkylaryl structures.

These 13-(substituted mercapto) tetracyclines are known in the art as tetracyclines possessing antimicrobial activity in and of themselves against a variety of gram-positive bacteria. This class of tetracyclines, its conventionally recognized pharmacological activity, and methods for its synthesis are described within U.S. Pat. No. 3,165,531, the text of which is expressly incorporated by reference herein.

In one embodiment, the preferred compositions, as empirically demonstrated hereinafter, are S-substituted alkyl derivatives at the No. 13 carbon ranging from 1–10 carbon atoms in length. Nevertheless, it is expected that a wide variety of RCO, RCX where X is a halogen, $RHC_2$, and $NRHC_2$ analogue and derivative forms in linear, branched, or cyclic structural format would be useful and operative in the present methodology in varying degrees. Accordingly, all such embodiments are deemed to be within the scope of Formulation I above.

As representative examples of the preferred embodiments of this class which were empirically evaluated, some preferred 6-deoxy-13-(substituted mercapto) tetracyclines (hereinafter "13-S-Derivatives") and their respective blocking activities are provided within Table II below. The $K_i$ represents the relative inhibitory activity of each compound. The lower the $K_i$, the more activity against the efflux protein. The preferred compound will have a lower $K_i$ than tetracycline (i.e., lower than about 4–8 μg/ml).

TABLE II

BLOCKING ACTIVITY OF 13-S-DERIVATIVES OF METHACYCLINE

| 13-S-Derivatives | Number of Carbon Atoms | $K_i$ (µg/ml)[1] |
|---|---|---|
| Decyl | 10 | 8.0 |
| Hexyl | 6 | 3.1 |
| Cyclohexyl | 6 | 0.4 |
| Benzyl | 7 | 0.9 |
| p-Cl-Benzyl | 7 | 1.5 |
| p-Me-Benzyl | 8 | 1.2 |
| Cyclopentyl, 2-morpholinomethyl | 5 | 0.5 |
| Cyclopentyl | 5 | 0.2 |
| Butyl | 4 | 0.5 |
| t-Butyl | 4 | 0.3 |
| Isobutyl | 4 | 0.1 |
| Propyl | 3 | 0.4 |
| Isopropyl | 3 | 0.4 |
| Dihydroxypropyl | 3 | 3.9 |
| Ethyl | 2 | 0.4 |

[1] By everted membrane vesicle assay.

From this representative listing, it will be noted that the shorter chain length substitutions or smaller adducts (cyclohexyl vs. hexyl; isobutyl vs. butyl; benzyl vs. parachlorobenzyl) are preferred inhibitors of the efflux system. Also, substitutions at the C2 position have only a small effect on the blocking activity. These results lead to a general conclusion that the activity of compositions having substitutions at the 13th carbon relate more to the size of the molecule than to the charge despite the presence of the sulfur atom. The longer chain length substitutions at the 13th carbon atom (e.g., decyl and hexyl) are not as active as the shorter length substitutions (e.g., butyl, propyl, and ethyl). Furthermore, the dihydroxypropyl derivative behaves more poorly in the blocking assay than the propyl or isopropyl derivative forms. On this basis, therefore, it is expected that a most preferred composition would be one having mercapto-substitutions on the 13th carbon atom in which the elipsoidal volume of the substituent joined to the sulfur atom is in the approximate size range of that provided by the butyl, benzyl or cyclopentyl derivatized structures.

Moreover, the data of Table II suggest that the administration to a resistant cell of a 13-substituted mercaptan derivative or a composition which appears structurally similar to a 13-substituted mercaptan derivative would effectively block the resistance mechanism of the cell; and allow the concomitant administration of another tetracycline, tetracycline analogue, or tetracycline derivative to effectively inhibit further cell growth.

In another embodiment, the blocking agent which can be employed in practicing the present invention is the class of C5 esters of tetracyclines of the formula (Formula II):

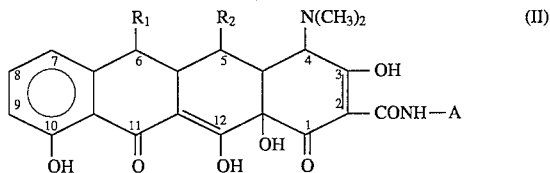

wherein $R_1$ and $R_2$ are selected from the group consisting of a methylene group, hydroxyl, hydrogen or a group consisting of organic entities comprising from 1–12 carbon atoms, with or without other heteroatoms including sulfur, oxygen, halogen, nitrogen, and the like, and takes form as linear, branched, or cyclic alkyl, aryl, or alkylaryl structures; and A is selected from the group consisting of a hydrogen atom, a methylene group, and any linear, branched, or ring structure comprising from 1–6 carbon atoms and optionally including heteroatoms such as oxygen and nitrogen atoms. Certain C5 esters have been described by Bernardi et al. (Il Farmaco, Ed. Sc. vol. 29—fasc. 12, pages 902–909(1974)) as being useful against, for example. S. aureus. Methods of synthesizing these disclosed derivatives may be found, for example, in U.S. Pat. No. 3,579,564, the disclosure of which is incorporated by reference herein.

In yet another embodiment, hybrids of the above-described 6-deoxy-13(substituted mercapto) and C5 ester may be employed as the blocking agent against resistant gram negative strains or alone against resistant gram positive strains.

In general, the synthesis of these 13-thio-substituted-5-acy-6-deoxy-tetracyclines (hereinafter "13,5 derivatives) may be accomplished by the anti-Markovnikov radical addition of alkyl or aryl thiols to the 6,13 exocyclic double bond of methacycline by the method of Blackwood et al., J. Am. Chem. Soc., 85:3943 (1963) the disclosure of which is incorporated by reference herein, followed by esterification with an appropriate carboxylic acid in anhydrous HF according to the method of Bernardi et al., Il Farmaco Ed. Sc., 29:9022 (1974) the disclosure of which is incorporated by reference herein, as depicted in Scheme I below.

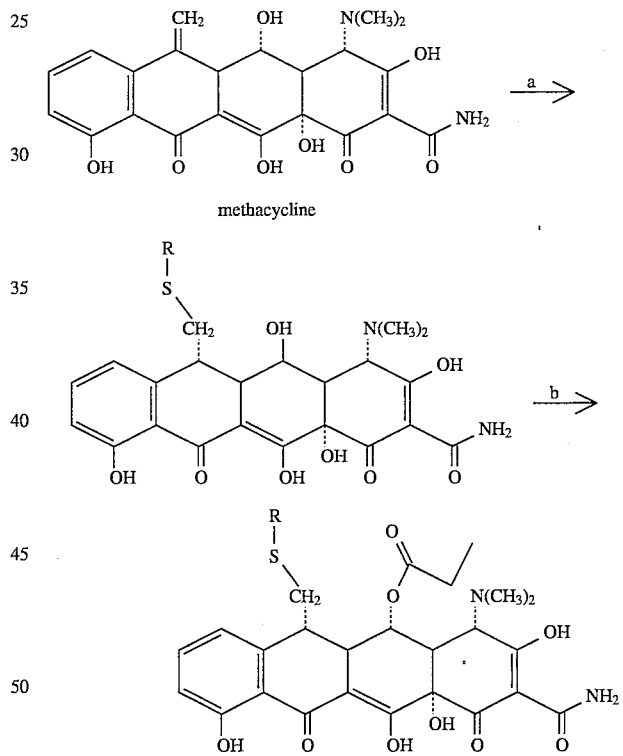

R = propyl or cyclopentyl
[a] (a)(i) RSH, where R = propyl, cyclopentyl (ii) AIBN; (b) anhydrous HF, carboxylic acid

FORMULATION, STRUCTURE, AND RANGE OF OTHER TETRACYCLINES, TETRACYCLINE ANALOGUES, AND TETRACYCLINE DERIVATIVE FORMS

The present invention requires that at least one other composition which is not chemically a blocking agent, such as the above-described 6-deoxy-13-(substituted mercapto)tetracycline or C5 ester, be administered concurrently or simultaneously with the blocking agent to the cell. This additional administered composition is any "tetracycline-type antibiotic" currently known which includes tetracycline itself; or any member of the tetracycline family including all analogues and derivatives which are NOT C5 ester derivatives nor 13-carbon substituted mercaptan compounds. Accordingly, the broadest definition for the additional tetracycline, analogue, or derivative to be administered concurrently is defined by Formula III below.

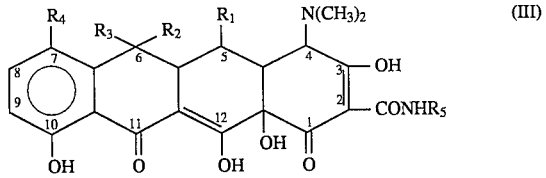

wherein $R_1$–$R_5$ may be a hydrogen atom, a halogen atom, a hydroxyl group, or any other organic composition comprising from 1–8 carbon atoms and optionally include a heteroatom such as nitrogen, oxygen, in linear, branched, or cyclic structural formats. A very wide range and diversity of embodiments within the definition of Formula III as are described within *Essentials of Medicinal Chemistry*, John Wiley and Sons, Inc., 1976, pages 512–517, the text of which is expressly incorporated by reference herein. Preferably $R_1$ and $R_2$ are hydrogen or a hydroxyl group; $R_3$ is a hydrogen or a methyl group; $R_4$ is a hydrogen atom, a halogen, or a nitrogen containing entity; and $R_5$ is a hydrogen atom, or a nitrogen containing ring structure. The commonly known tetracycline analogues and derivatives including the following: oxytetracycline; chlortetracycline; demeclocycline; doxycycline; chelocardin; minocycline; rolitetracycline; lymecycline; sancycline; methacycline; apicycline; clomocycline; guamecycline; meglucycline; mepyclycline; penimepicycline; pipacycline; etamocycline; and penimocycline. It will be recognized and appreciated that these specific tetracycline compositions (as well as many others conventionally known and available through the scientific literature or from commercial sources) may be employed as the alternative tetracycline-type composition which does not contain a C5 ester nor a 13-carbon substituted mercapto group as part of its formulation and chemical structure.

The individual compositions embodying Formula I, 13-S-derivatives, or Formula II, C5 esters, or the 13,5 derivative, and Formula III, alternative tetracycline compounds, can be administered concurrently, sequentially or simultaneously in any appropriate carrier for oral, topical or parenteral administration. It is also possible that the two discrete compositions could be linked covalently or otherwise joined to each other and/or to other ligands. These compositions can be introduced by any means that affects an infectious or disease state caused by tetracycline-resistant microorganisms in humans and/or animals. The specific route of administration, the choice of carrying materials, and the particular means for introducing each composition concomitantly to the tetracycline-resistant cells are of no major importance or relevance.

Accordingly, if the 13-S-derivative, the C5 derivative composition or the 13,5 derivative and the other alternative tetracycline-type compound are to be applied topically, they can be individually or mutually admixed in a pharmacologically inert topical carrier such as a gel, an ointment, a lotion, or a cream. Such topical carriers include water, glycerol, alcohol, propylene glycol, fatty alcohols, triglycerides, fatty acid esters, or mineral oils. Other possible topical carriers are liquid petrolatum, isopropylpalmitate, polyethylene glycol, ethanol 95%, polyoxyethylene monolauriate 5% in water, sodium lauryl sulfate 5% in water, and the like. In addition, materials such as anti-oxidants, humectants, viscosity stabilizers, and the like may also be added if and when necessary.

Similarly, if the 13-S-derivative, the C5 derivative composition or the 13,5 derivative and the alternative tetracycline-type composition are to be introduced concurrently, sequentially or simultaneously in parenteral form, each composition will be prepared individually or in combination in sterile form; in multiple or single dose formats; and be dispersed in a fluid carrier such as sterile physiological saline or 5% dextrose solutions commonly used with injectables.

Furthermore, if the present methodology is to be employed for oral administration, each of the two requisite compositions may be provided individually or in combination in the form of prepared capsules, cachets, or tablets each containing a predetermined quantity of the 13-S-derivative, the C5 ester composition or the 13,5 derivative and the tetracycline-type antibiotic. Their preparation may also take form as a powder or granules; or dissolved or suspended in a solution or suspension within an oil-in-water emulsion or conversely within a water-in-oil liquid emulsion for ingestion or for oral cavity lavage treatments. These solid or liquid formulations may generally include one or more carrier materials such as flavoring agents, binders, buffers, diluents, surface active agents, thickeners, lubricants, preservatives, and the like. It is deemed that all of these methods for formulating, preparing, and administering the requisite compositions are conventionally known.

The effective dosages to be employed in vivo are typically dictated by the intended application or use circumstances; and are generally decided by reconciling several different factors. First, it will be recognized and appreciated that each embodiment of the 13-S-derivative, the C5 derivative composition or the 13,5 derivative and each embodiment of the alternative tetracycline composition (analogue or derivative) will have individual specific pharmacological activity which can be represented and evaluated as the Minimal Inhibitory Concentration (hereinafter "MIC") and as the Minimal Lethal Concentration (hereinafter "MLC")—each of which varies with its specific formulation and chemical structure. Second, any given specific chemical formulation will also have varying MIC and MLC dosages which fluctuate with the cell type—as, for example, with the genus and species of microorganism; thus, the MIC and MLC of each individual composition will vary markedly—as, for example, when administered to gram-positive bacteria in comparison to gram-negative bacteria or to the various different genera of fungi, rickettsia, and parasites. Thirdly, the degree of tetracycline resistance is known to very substantially among the different cell types, their delineated genera, and among the different species comprising a single genus; this varying degree of tetracycline resistance is without regard to whether the mechanism of resistance is based upon an active efflux system or a ribosome protection system intracellularly. Lastly, each specific route of in vivo administration is conventionally recognized to require markedly different dose concentration of conventionally known tetracycline compounds; accordingly, in vivo therapeutic dosages will vary depending upon whether the tetracycline-type composition is given orally, parenterally, or topically. Each of these individual factors should be taken in consideration by the user when deciding the proper dosage or concentration for the 13-S-derivative, the C5 derivative composition or the 13,5 derivative and the other tetracycline antibiotic composition.

In general, however, it is most desirable that the dosage and concentration of the 13-S-derivative, the C5 derivative composition (broadly defined by Formula I or Formula II respectively) or the 13,5 derivative be administered in a subinhibitory quantity—that is, less than the minimum inhibitory quantity—that is, less than the minimum inhibitory concentration or the minimum lethal concentration for that specific composition when employed against a tetracycline-resistant cell. In comparison, it is essential that the chosen alternative tetracycline-type composition (tetracycline analogue or tetracycline derivative meeting the broad definitional requirements of Formula III above) be employed in at least a minimum inhibitory concentration; and preferably be administered at an effective dosage to provide a minimal lethal concentration in-situ. Accordingly, it is deemed that the concentrations for the two concomitantly administered compositions are conventionally known within the art; and can be optimized with a minimum of difficulty.

Again, as noted above, certain novel compounds, in particular, the 13,5 derivatives, have been found to be particularly useful against certain gram positive bacteria when administered alone.

In this context, and as empirically demonstrated by the data of Charts 1–5 for the 13-S-derivatives, Charts 6–7 for the C-5 derivatives and Charts 8–9 for the 13,5 derivatives which follow hereinafter, the concomitant administration of the 13-S-derivative, the C5 derivative composition or the 13,5 derivative and the other tetracycline-type composition together provides not only means for overcoming tetracycline resistance but also offers the capability to enhance the pharmacological activity of the known tetracycline-type composition to exert cidal activity and cidal effects upon the cell. Contrary to the universally accepted conventional view that tetracyclines, regardless of formulation, are only bacteriostatic agents—i.e., agents that do not kill but only inhibit future growth, the present method provides a synergistic combination of compositions which enhances the antibiotic activity of the tetracycline-type composition; and, for the first time, allows the enhanced tetracycline-type composition to exert bacteriocidal powers, "cidal" capability, i.e., the ability to kill the cell rather than merely inhibit its growth, against a broad spectrum of bacteria.

In addition, the general molar ratio of 13-S-derivative, the C5 derivative composition, or the 13,5 derivative to alternative tetracycline-type composition is expected generally to be from 0.01:100.0, and is preferably in the range from 0.05:2.0. It is most desirable, however, that in no instance should the dosage of the 13-S-derivative, the C5 derivative composition or the 13,5 derivative be employed in a concentration which is within the MIC or MLC values. In comparison, the alternative, tetracycline-type composition (tetracycline or tetracycline analogue or tetracycline derivative) should be administered in accordance with conventional practice for the efficacious therapeutic treatment of infection or disease in humans and/or animals. Accordingly, for therapeutic purposes, the daily dosage of 13-S-derivative, the C5 derivative composition or the 13,5 derivative for treatment of disease in living mammals is expected to lie in the range from 0.01–100 mg/kg (preferably from 15 to 30 mg/kg) of normal body weight while the dosage of the other tetracycline, analogue or derivative should continue to be given in the range from 500 milligrams to 2.0 grams per day depending upon the age, weight, and route of administration. When the 13,5 derivative is administered alone, for example, for treating infections caused by gram positive bacteria such as *S. aureus* or *E. faecalis*, the dosage employed is preferably that used in conventional tetracycline therapy.

It will also be understood that the normal, conventionally known, precautions will be taken regarding the administration of tetracyclines generally in order to ensure their efficacy under normal use circumstances. Especially when employed for therapeutic treatment of humans and animals in vivo, the practitioner should take all sensible precautions to avoid conventionally known contradictions and toxic effects. Thus, the conventionally recognized adverse reactions of gastrointestinal distress and inflammations, the renal toxicity, hypersensitivity reactions, changes in blood, and impairment of absorption through aluminum, calcium, and magnesium ions should be duly considered in the conventional manner.

MODE AND MANNER OF PHARMACOLOGICAL ACTIVITY

It must be emphasized again that the present methodology is useful with all cells, regardless of type, source, family, genus, or species which have genetic determinants for tetracycline resistance. The methodology of the present invention is suitable for use with both tetracycline resistance attributable to an active efflux transport system utilizing one or more TET proteins which actively bind with tetracycline-type antibiotics and transport the tetracycline composition out of the cytoplasm of the cell; and also with tetracycline resistance which is a nonefflux system and typically involves a ribosome protection mechanism which causes a tetracycline antibiotic to fail to inhibit protein synthesis intracellularly. Regardless of which tetracycline resistance mechanism is present within the resistant cell, the present methodology is effective in overcoming tetracycline resistance and in rendering the cell tetracycline-sensitive. Although the sequence of molecular reactions remains far from understood at the present time, the concurrent or simultaneous administration of at least one 13-S-derivative or the C5 derivative composition prepared in accordance with Formula I or Formula II or the 13,5 derivative and at least one other tetracycline antibiotic composition in accordance with Formula III causes an in situ conversion of the cell from a resistant state into a tetracycline-sensitive state.

The efficacy and utility of the present methodology is based upon the cell's unexpected preferential reaction with the 13-S-derivative, the C5 derivative composition or the 13,5 derivative which is desirably present in a subinhibitory concentration; and the comparable absence of avidity by the cell for the other tetracycline-type composition concomitantly administered. The resistance mechanism of the cell— be it the active efflux system or the ribosome protection system—focuses upon and interacts with the 13-S-derivative, the C5 derivative composition or the 13,5 derivative primarily and predominantly; the concurrent or simultaneous presence of the other tetracycline-type antibiotic composition is relatively ignored and effectively overlooked by the tetracycline-resistance mechanism of the cell.

Consequently, the other tetracycline-type antibiotic composition is allowed to accumulate intracellularly in at least a minimum inhibitory concentration (and preferably in a minimum lethal concentration); and this other tetracycline-type antibiotic is able to bind to the ribosomes and to exert its recognized pharmacological activity intracellularly to prevent further protein synthesis within that cell. In this respect, the administered 13-S-derivative of Formula I or C5 derivative composition of Formula II or 13,5 derivative is clearly the preferred composition for reaction with the tetracycline-resistance mechanism present; and by this preferred reactivity, acts as a blocking agent to engage and to divert the tetracycline resistance mechanism of that cell to the extent that the concurrently or simultaneously administered other tetracycline-type antibiotic composition of Formula III is able to exert its characteristic pharmacological activity efficaciously against the cell and to prevent further protein synthesis intracellularly. The present methodology is thus effective and useful by the cell's own preference for engagement and reaction with the 13-S-derivative, the C5 derivative composition or the 13,5 derivative, rather than with the concomitantly administered other tetracycline-type antibiotic. In this manner, the cumulative effect is to render the cell tetracycline-sensitive for therapeutic purposes.

EXPERIMENTAL STUDIES

A series of experiments and resulting empirical data demonstrate and evidence the efficacy and utility of the present invention. These experiments will illustrate the essential components of the present methodology, and will demonstrate the value of the preferred embodiments comprising 13-S- or C5 derivative compositions prepared in accordance with Formula I, or Formula II and document the range and diversity of some tetracycline-resistant microorganisms which can be rendered sensitive to tetracycline therapy by employing the present methodology.

For purposes of conducting the experimental model, tetracycline for the 13-S-derivative or doxycycline for the C5 derivative was employed uniformly in combination with a variety of different C5 or 13 substituted mercapto-tetracyclines. Nevertheless, it will be understood that doxycycline and tetracycline are employed merely as a representative of all the different compositions and embodiments of tetracyclines, tetracycline analogues, and tetracycline derivatives conforming to the definition of Formula III given previously; and that the present invention is not limited to the use of tetracycline alone as a specific chemical formulation and structure. Moreover, it will be understood that the experiments and empirical data presented hereinafter are merely illustrative examples of the present invention without regard to specific applications or particular uses; and that the described experiments are merely representative of the totality of embodiments encompassed within the scope of the present invention.

EXPERIMENTAL SERIES 1

Initially, the inhibitory effects of a variety of different 13-S-derivatives in comparison to tetracycline and minocycline were examined using a variety of different bacteria. These included tetracycline sensitive (hereinafter "Tc$^s$") and tetracycline resistant (hereinafter "Tc$^r$") strains of *E. coli*, *S. aureus*, and *E. faecalis*. The general protocol for performing these experiments is as follows: Cultures were grown up fresh in L broth in the morning from an overnight culture. After 4–6 hours of growth, each bacterial culture was diluted to an $A_{530}$ of 0.2–0.5 depending on the strain (*E. coli*, 0.5; *S. aureus*, 0.4; *E. faecalis*, 0.2). Individual tubes, containing 1 ml of L broth and different concentrations of 13-S-derivatives, were inoculated with the different bacterial cultures and then incubated at 37° C. After 17–18 h of incubation, the concentration of each 13-S-derivative at which no observed cloudiness was seen was called the minimal inhibitory concentration (MIC). The minimal lethal concentration (MLC), i.e., that concentration which kills 99.9%, was based on the number of bacteria initially inoculated into the assay tubes. Those culture tubes showing no bacterial growth after incubation at 37° C. were evaluated for the number of bacteria remaining.

The results obtained in this experimental series are provided by Tables E1–E3 below.

TABLE E1

SUSCEPTIBILITY TESTING OF *E. coli*

| Drug | Tc$^s$ (MI308–225) | | Class A Tc$^r$ (DI-299) | | Class B Tc$^r$ (DI-209) | |
|---|---|---|---|---|---|---|
| | MIC (µg) | MLC (µg) | MIC (µg) | MLC (µg) | MIC (µg) | MLC (µg) |
| Tetracycline | 0.6 ± 0.25 | 40 ± 0.25 | 160 ± 0.25 | 200 | >200 | >200 |
| Minocycline | <4 | <4 | <4 | 20 | 6 ± 2 | 30 ± 10 |
| Benzyl* | 16 ± 6 | 25 ± 5 | 46 ± 20 | 160 ± 50 | 30 ± 0.25 | 90 ± 10 |
| Cyclohexyl* | 60 ± 10 | 120 | 100 ± 0.25 | >200 | ND | ND |
| Cyclopentyl* | 20 | 60 | 40 ± 0.25 | 80 | 80 ± 40 | 100 ± 50 |
| Propyl* | 30 ± 5 | 60 ± 10 | 40 ± 0.25 | 60 | 60 | 80 |
| Isopropyl* | 22 ± 2 | 60 | 46 ± 6 | 60 | 35 ± 5 | 46 ± 16 |
| Ethyl* | 5 ± 0.25 | 60 | 14 ± 4 | 46 ± 6 | 35 ± 15 | 60 ± 10 |

*Note: ±0.25 indicates that the same MIC or MLC was determined in two or more experiments. Other values represent experimental error determined by averaging the values obtained in multiple experiments. If no value is given, the experiment has not be repeated. Larger numbers will consistently have larger errors since all experiments were done by the standard 1 ml serial dilution liquid MIC procedure.
ND = not done.
Tc$^s$ = tetracycline sesnsitive strain.
Tc$^r$ = tetracycline resistant strain.
$^a$S-mercapto derivative of methacycline.

TABLE E2

SUSCEPTIBILITY TESTING OF *S. aureus*

| Drug | Tc$^s$ (RN450) | | Tc$^r$ (RN4250) | |
|---|---|---|---|---|
| | MIC (µg) | MLC (µg) | MIC (µg) | MLC (µg) |
| Tetracycline | 0.75 ± 0.25 | >6 | 90 ± 10 | 100 |
| Minocycline | <0.25 | 8 | <0.25 | >80 |
| Benzyl | 0.2 ± 0.1 | 10 ± 2 | 1 ± 0.25 | 10 ± 4 |
| Cyclohexyl | 2.5 ± 1.25 | 10 ± 5 | 1.5 ± 0.5 | 10 ± 4 |
| Cyclopentyl | 1 | 5 | 2 ± 0.25 | 6 ± 2 |
| Propyl | 0.5 ± 0.25 | 5 | 4 ± 0.25 | 16 ± 4 |
| Isopropyl | 0.5 ± 0.25 | 6 ± 2 | 4.5 ± 0.5 | 8 |
| Ethyl | 0.5 ± 0.25 | 4 | 5 ± 2 | 30 ± 10 |

Tc$^s$ = tetracycline sensitive strain
Tc$^r$ = tetracycline resistant strain

TABLE E3

| | SUSCEPTIBILITY TESTING OF E. faecalis | | | | | |
|---|---|---|---|---|---|---|
| | $Tc^s$ (ATCC9790r) | | $Tc^r$ (L) ATCC9790r/TeIL) | | $Tc^r$ (M) (ATCC09790r/TeIM) | |
| Drug | MIC (μg) | MLC (μg) | MIC (μg) | MLC (μg) | MIC (μg) | MLC (μg) |
| Tetracycline | 0.25 | >200 | 90 ± 10 | >300 | 100 | 300 |
| Minocycline | <0.25 | >40 | <0.25 | >80 | 10 | >80 |
| Benzyl* | 0.5 ± 0.25 | 8 ± 0.25 | 0.75 ± 0.25 | 8 ± 2 | 3.5 ± 1 | 18 ± 2 |
| Cyclohexyl* | 1.25 ± 0.25 | 8 | 1.5 ± 0.5 | 8 ± 2 | 2.5 ± 0.5 | 10 ± 0.25 |
| Cyclopentyl* | 1 ± 0.25 | 10 ± 4 | 1 ± 0.5 | 18 ± 2 | 3 ± 1 | >16 |
| Propyl* | 1.6 ± 0.25 | 40 ± 0.25 | 2.5 ± 0.5 | 60 ± 10 | 16 ± 2 | 30 ± 10 |
| Isopropyl* | 3 ± 1 | 20 ± 0.25 | 3 ± 1 | 100 ± 0.25 | 22 ± 2 | >200 |
| Ethyl* | 1 ± 0.5 | 40 ± 0.25 | 4 ± 1 | 100 ± 0.25 | 25 ± 5 | >200 |

$Tc^s$ = tetracycline sensitive strain.
$Tc^r$ = tetracycline resistant strain.

A close inspection and reading of Tables E1–E3 will reveal the following points regarding the tetracycline susceptible strains and the tetracycline resistant strains tested. These are:

Susceptible Strains

1. E. coli (Table E1, Column 1)
    None of these compounds was more active than tetracycline or minocycline against susceptible E. coli strains. The most active was the ethyl-S-derivative which showed an MIC of 5 μg/ml.

2. S. aureus (Table E2, Column 1)
    Against susceptible S. aureus, all of the 13-S-derivatives were effective alone within therapeutic ranges. They were about as active as tetracycline and minocycline (except perhaps the cyclohexyl derivative). All 13-S-derivatives showed bacteriocidal activity better than tetracycline or minocycline of which 4 showed bacteriocidal activity at a level of about 5 μg/ml.

3. E. faecalis (Table E3, Column 1)
    Against susceptible Enterococcus faecalis, all the tested compositions were effective well within a therapeutic range and all, but the isopropyl derivative, at 1 μg/ml or less. All showed greater bacteriocidal activity than did tetracycline or minocycline, especially the benzyl, cyclohexyl, and cyclopentyl S-derivatives.

Resistant Strains

1. All the other compositions were more active than tetracycline against resistant E. coli strains (both Class A and Class B determinants). None individually was as active as minocycline. Most 13-S-derivatives showed bacteriocidal activity lower than tetracycline against resistant E. coli, but not within therapeutic ranges (Table E1, Columns 2 and 3).

2. Against resistant S. aureus, all the tested compounds showed an MIC within a therapeutic range, at least 20–100 fold more active than tetracycline. None individually was as active as minocycline. All 13-S-derivatives were more bacteriocidal than tetracycline or minocycline alone with cyclopentyl showing an MLC of 6±2 μg/ml. Benzyl, cyclohexyl, and cyclopentyl S-derivatives each showed similar MIC values and MLC values against susceptible and resistant S. aureus. The most active 13-S-derivative was the cyclopentyl form (Table E2, Column 2).

3. All the tested compositions had an MIC within a therapeutic range against E. faecalis bearing the Tet L determinant: benzyl>cyclopentyl>cyclohexyl, followed by the others. The 13-S-derivatives were equally effective by MIC against susceptible and Tet L containing Enterococcus. All were more bacteriocidal than tetracycline and minocycline individually; the MLC for benzyl and cyclohexyl was 8±2 μg/ml (Table E3, Column 2).

4. Against Tet M containing E. faecalis, all the other tested compounds were considerably more antibacterial than tetracycline. Three of them, the benzyl, cyclohexyl, and cyclopentyl derivatives also had MIC values below minocycline and within therapeutic levels (Table E3, Column 3). Bacteriocidal activity was observed, but above therapeutic levels.

5. While the MLC against resistant S. aureus and E. faecalis was 8–10 μg/ml for the most active drugs, a killing effect (seen as a 10–99% drop in cell viability) by the analogues occurred at considerably lower drug concentrations (see charts).

EXPERIMENTAL SERIES 2

Subsequently, another series of experiments was conducted which employed concurrent administrations of tetracycline and at least one other 13-S-derivative composition in accordance with Formula I above. The general experimental protocol for synergy studies followed substantially that procedure employed for the standard MIC and MLC assays. The organisms were grown in fresh L broth and inoculated in culture tubes containing diffęrent concentrations of 13-S-derivative compositions and tetracycline together. The previously described methods for determining MIC and MLC were otherwise followed.

Accordingly, the results are provided by Charts 1–5 in which: Chart 1 represents the concurrent administration of 13-cyclopentyl sulfide derivative of methacycline in varying proportional ratios to tetracycline; Chart 2 represents 13-propyl-sulfide derivatives of methacycline varying proportional ratios with tetracycline; Chart 3 represents varying proportional ratios with tetracycline; Chart 3 represents varying proportional ratios of 13-cyclohexyl-sulfide derivatives of methacycline and tetracycline administered concurrently; Chart 4 represents varying proportional ratios of 13-benzyl-sulfide derivatives of methacycline delivered concurrently with tetracycline; and Chart 5 illustrates the concurrent administration of varying proportions of 13-ethyl-sulfide derivatives of methacycline and tetracycline.

CHART 1

MIC/MLC (μg/ml) dosages for tetracycline-resistant strains using cyclopentyl-sulfide derivatives of methacycline with and without tetracycline Strain: *E. coli* (D1-299)

| Tc/A | 0 | 4 | 8 | 16 | 32 |
|---|---|---|---|---|---|
| 0 | * | * | * | * | * |
| 2 | * | * | + | ↓ | ▓ |
| 4 | * | 0 | 0 | ▓ | ▓ |
| 8 | * | ↓ | ▓ | ▓ | ▓ |
| 16 | * | ↓ | ▓ | ▓ | ▓ |

Strain: *S. aureus* (RN4250)

| Tc/A | 0 | 1 | 2 | 4 | 8 |
|---|---|---|---|---|---|
| 0 | * | * | 0 | ↓ | ▓ |
| 1 | * | + | ↓ | ▓ | ▓ |
| 2 | * | + | ↓ | ▓ | ▓ |
| 4 | * | 0 | ↓ | ▓ | ▓ |
| 8 | * | 0 | ↓ | ▓ | ▓ |

Strain: *E. faecalis* (Tet L)

| Tc/A | 0 | 1 | 2 | 4 | 8 |
|---|---|---|---|---|---|
| 0 | * | 0 | ↓ | ↓ | ↓ |
| 1 | * | 0 | ↓ | ↓ | ↓ |
| 2 | * | 0 | ↓ | ↓ | ↓ |
| 4 | * | 0 | ↓ | ↓ | ↓ |
| 8 | * | 0 | ↓ | ↓ | ↓ |

Strain: *E. faecalis* (Tet M)

| Tc/A | 0 | 2 | 4 | 8 | 16 |
|---|---|---|---|---|---|
| 0 | * | * | 0 | ↓ | ↓ |
| 2 | * | * | 0 | 0 | ↓ |
| 4 | * | * | 0 | 0 | ↓ |
| 8 | * | * | 0 | ↓ | ↓ |
| 16 | * | * | 0 | ↓ | ↓ |

Note:
* Growth;
0 No Growth (MIC);
↓ Killing;

 99.9% Killing (MLC).

Tc = tetracycline concentration (μg/ml).
A = 6-deoxy-13-(cyclopentyl mercapto) tetracycline concentration (μg/ml)

CHART 2

MIC/MLC (µg/ml) dosages for tetracycline-resistant strains
using propyl-sulfide derivatives of methacycline with and without tetracycline Strain: *E. coli* (D1-299)

| Tc/B | 0 | 4 | 8 | 16 | 32 |
|---|---|---|---|---|---|
| 0 | * | * | * | * | 0 |
| 4 | * | * | 0 | ↓ | ▓ |
| 8 | * | ↓ | ↓ | ▓ | ▓ |
| 16 | * | ▓ | ▓ | ▓ | ▓ |
| 32 | * | ▓ | ▓ | ▓ | ▓ |

Strain: *S. aureus* (RN4250)

| Tc/B | 0 | 2 | 4 | 8 | 16 |
|---|---|---|---|---|---|
| 0 | * | * | ↓ | ↓ | ↓ |
| 2 | * | + | ↓ | ↓ | ↓ |
| 4 | * | 0 | ↓ | ↓ | ↓ |
| 8 | * | 0 | ↓ | ↓ | ↓ |
| 16 | * | ↓ | ↓ | ↓ | ↓ |

Strain: *E. faecalis* (Tet L)

| Tc/B | 0 | 2 | 4 | 8 | 16 |
|---|---|---|---|---|---|
| 0 | * | 0 | 0 | ↓ | ↓ |
| 2 | * | 0 | 0 | ↓ | ↓ |
| 4 | * | 0 | 0 | ·↓ | ↓ |
| 8 | * | 0 | ↓ | ↓ | ↓ |
| 16 | * | ↓ | ↓ | ↓ | ↓ |

Strain: *E. faecalis* (Tet M)

| Tc/B | 0 | 4 | 8 | 16 | 32 |
|---|---|---|---|---|---|
| 0 | * | * | * | ↓ | ↓ |
| 4 | * | * | * | ↓ | ↓ |
| 8 | * | * | + | ↓ | ↓ |
| 16 | * | * | 0 | ↓ | ↓ |
| 32 | * | * | 0 | ↓ | ↓ |

Note:
* Growth;
0 No Growth (MIC);
↓ Killing;
 99.9% Killing (MLC).

Tc = tetracycline concentration (µg/ml).
B = 6-deoxy-13-(propyl mercapto) tetracycline concentration (µg/ml)

CHART 3

MIC/MLC (µg/ml) dosages for tetracycline-resistant strains
using cyclohexyl-sulfide derivatives of methacycline with and without tetracycline Strain: *E. coli* (D1-299)

| Tc/C | 0 | 5 | 10 | 20 | 40 |
|---|---|---|---|---|---|
| 0 | * | * | * | * | * |
| 25 | * | * | + | ↓ | ↓ |
| 5 | * | 0 | ↓ | ▓ | ▓ |
| 10 | * | ↓ | ↓ | ▓ | ▓ |
| 20 | * | ↓ | ▓ | ▓ | ▓ |

Strain: *S. aureus* (RN4250)

| Tc/C | 0 | 1 | 2 | 4 | 8 |
|---|---|---|---|---|---|
| 0 | * | ↓ | ▓ | ▓ | ▓ |
| 1 | * | ↓ | ▓ | ▓ | ▓ |
| 2 | * | ↓ | ▓ | ▓ | ▓ |
| 4 | * | ▓ | ▓ | ▓ | ▓ |
| 8 | * | ▓ | ▓ | ▓ | ▓ |

CHART 3-continued

| Strain: E. faecalis (Tet L) | | | | | |
|---|---|---|---|---|---|
| Tc/C | 0 | 1 | 2 | 4 | 8 |
| 0 | * | 0 | ↓ | ↓ | ↓ |
| 1 | * | 0 | ↓ | ↓ | ▓ |
| 2 | * | 0 | ↓ | ↓ | ▓ |
| 4 | * | 0 | ↓ | ↓ | ▓ |
| 8 | * | 0 | ↓ | ▓ | ▓ |

| Strain: E. faecalis (Tet M) | | | | | |
|---|---|---|---|---|---|
| Tc/C | 0 | 25 | 5 | 10 | 20 |
| 0 | * | 0 | ↓ | ▓ | ▓ |
| 25 | * | 0 | ↓ | ▓ | ▓ |
| 5 | * | 0 | ↓ | ▓ | ▓ |
| 10 | * | 0 | ↓ | ↓ | ▓ |
| 20 | * | ↓ | ↓ | ↓ | ▓ |

Note:
* Growth;
0 No Growth (MIC);
↓ Killing;

 99.9% Killing (MLC).

Tc = tetracycline concentration (μg/ml).
C = 6-deoxy-13-(cyclohexyl mercapto) tetracycline concentration (μg/ml)

CHART 4

MIC/MLC (μg/ml) dosages for tetracycline-resistant strains
using benzyl-sulfide derivatives of methacycline with and without tetracycline

| Strain: E. coli (D1-299) | | | | | |
|---|---|---|---|---|---|
| Tc/D | 0 | 4 | 8 | 16 | 32 |
| 0 | * | * | * | + | ↓ |
| 4 | * | * | ↓ | ↓ | ▓ |
| 8 | * | * | ↓ | ↓ | ▓ |
| 16 | * | ↓ | ↓ | ↓ | ▓ |
| 32 | * | ↓ | ↓ | ▓ | ▓ |

| Strain: S. aureus (RN4250) | | | | | |
|---|---|---|---|---|---|
| Tc/D | 0 | 1 | 2 | 4 | 8 |
| 0 | * | ↓ | ↓ | ↓ | ↓ |
| 1 | * | ↓ | ↓ | ↓ | ▓ |
| 2 | * | ↓ | ↓ | ▓ | ▓ |
| 4 | * | ↓ | ▓ | ▓ | ▓ |
| 8 | * | ↓ | ▓ | ▓ | ▓ |

| Strain: E. faecalis (Tet L) | | | | | |
|---|---|---|---|---|---|
| Tc/D | 0 | 1 | 2 | 4 | 8 |
| 0 | * | ↓ | ↓ | ↓ | ↓ |
| 1 | * | ↓ | ↓ | ↓ | ↓ |
| 2 | * | ↓ | ↓ | ↓ | ↓ |
| 4 | * | ↓ | ↓ | ↓ | ↓ |
| 8 | * | ↓ | ↓ | ▓ | ▓ |

| Strain: E. faecalis (Tet M) | | | | | |
|---|---|---|---|---|---|
| Tc/D | 0 | 2 | 4 | 8 | 16 |
| 0 | * | 0 | ↓ | ↓ | ↓ |
| 2 | * | 0 | ↓ | ↓ | ↓ |
| 4 | * | 0 | ↓ | ↓ | ↓ |
| 8 | * | ↓ | ↓ | ↓ | ↓ |
| 16 | * | ↓ | ↓ | ↓ | ↓ |

Note:
* Growth;
0 No Growth (MIC);
↓ Killing;

 99.9% Killing (MLC).

Tc = tetracycline concentration (μg/ml).
D = 6-deoxy-13-(benzyl mercapto) tetracycline concentration (μg/ml)

CHART 5

MIC/MLC (μg/ml) dosages for tetracycline-resistant strains
using ethyl-sulfide derivatives of methacycline with and without tetracycline Strain: *E. coli* (D1-299)

| Tc/E | 0 | 2 | 4 | 8 | 16 |
|---|---|---|---|---|---|
| 0 | * | * | * | * | 0 |
| 2 | * | * | * | 0 | ↓ |
| 4 | * | * | 0 | ↓ | ↓ |
| 8 | * | * | ↓ | ↓ | ▓ |
| 16 | * | ↓ | ↓ | ↓ | ▓ |

Strain: *S. aureus* (RN4250)

| Tc/E | | | | | |
|---|---|---|---|---|---|
| | | | | | |

Strain: *E. faecalis* (Tet L)

| Tc/ | | | | | |
|---|---|---|---|---|---|
| | | | | | |

Strain: *E. faecalis* (Tet M)

| Tc/ | | | | | |
|---|---|---|---|---|---|
| | | | | | |

Note:
* Growth;
0 No Growth (MIC);
↓ Killing;
▓ 99.9% Killing (MLC).
Tc = tetracycline concentration (μg/ml).
E = 6-deoxy-13-(ethyl mercapto) tetracycline concentration (μg/ml)

As evidenced by the data of Charts 1–5, the results of administering 13-S-derivative tetracycline compositions concurrent with varying proportional ratios of tetracycline clearly support the following conclusions:

1. Against the tetracycline resistant (Class A) *E. coli* (strain D1-299) synergy was observed. The most effective analogues were cyclopentyl, cyclohexyl, and ethyl. These all inhibited growth at concentrations of 5 μg/ml or less of analogue and tetracycline. Synergy was also demonstrated in bacteriocidal activity, although the amounts of the 13-S-derivatives needed were higher than 5 μg/ml in order to kill 99.9% of the cells with 4–5 μg/ml of tetracycline.

2. Against tetracycline resistant *S. aureus*, all the 13-S-derivatives tested showed synergistic activity at levels of both drugs below 4 μg/ml. In addition, cyclohexyl>cyclopentyl>benzyl showed bacteriocidal activity within therapeutic combinations with tetracycline where the combined dose of the two drugs was ≦6 μg/ml to achieve MLC.

3. Against *E. faecalis* (Tet L), all four 13-S-derivatives showed excellent synergy in inhibiting growth in combination: <1 μg/ml of analogue with 1 μg/ml tetracycline. While bacteriocidal effects were seen synergistically, the amounts of drugs needed to produce the MLC were higher than each at 4–5 μg/ml.

4. Against *E. faecalis* (Class M) cyclopentyl, cyclohexyl, and benzyl S-derivatives showed little, if any synergistic activity with tetracycline. However, the propyl-S-derivative, while not as active alone, did show meaningful synergy.

SUMMARY

1. These studies show that a group of S-alkyl substitutions and the benzyl substitution at the 13th carbon position of methacycline can inhibit growth of both susceptible and tetracycline resistant gram-positive (and to a less extent gram-negative) organisms.

2. In combination with tetracycline, all of these 13-S-derivatives show synergy, both in growth inhibition and in bacteriocidal activity for gram-positive as well as gram-negative susceptible and resistant strains.

3. All of the 13-S-derivatives tested show bacteriocidal activity, although this is most evident against the gram-positive bacteria tested alone and in synergy with tetracycline, and against *E. coli* in synergy with tetracycline.

4. All the 13-S-derivatives tested alone show greater bacteriocidal activity than minocycline against *S. aureus* and *E. faecalis*, chiefly the benzyl, cyclohexyl, and cyclopentyl derivatives.

EXPERIMENTAL SERIES 3

Everted vesicles, to which the TET proteins responsible for tetracycline efflux are attached, provide a reliable method for measuring efflux from tetracycline-resistant bacteria. By exposing the vesicles to different concentrations of tetracycline and measuring the amount of tetracycline taken up by the vesicle, the affinity of tetracycline for the efflux system may be determined. Similarly, exposure of the vesicles to solutions having both tetracycline and a potential efflux protein blocking agent produces a competition between tetracycline and the blocking agent for the limited number of binding states on the TET proteins. Subsequent measurement of the tetracycline concentration within the everted vesicles thus provides a sound measurement of the function of the bacterial efflux system for tetracycline in the presence of the potential blocking agent. This assay has also identified agents which affect resistance specified by other mechanisms, namely by a cytoplasmic protein which protects ribosomes from the inhibition of tetracycline (see U.S. Pat. No. 5,064,821).

In the experiments, 0.5 mg/ml of everted membrane vesicles of *E. coli* strain D1-209 bearing the Class B tetracycline resistance determinant were incubated with about 4 µM of $^3$H-tetracycline in a volume of 300 µl. Different potential blocking agents with substitutions at the C5 position were separately tested at concentrations of 0.2, 0.5 and 2 µg/ml. A control experiment, wherein no blocking agent was used, was also performed. After incubation for 2.5 minutes, the vesicles were collected on membrane filters and the effect of the blocking agent on uptake of $^3$H-tetracycline was assessed by liquid scintillation counting of the radioactivity on the filters.

The assay showed the relative inhibition of tetracycline by the different drugs vis a vis drug amounts (Table E4 below). Using the uptake at 2.5 minutes (when the system reaches equilibrium) the IC$_{50}$ of the analogs was determined. Using this method, the IC$_{50}$ of different C5 esters ranged from 0.2 µM (5 proprionate methacycline) to 9.4 µM (5 cyclopropanoate methacycline). Some showed no effect in this assay, suggesting they have poor, if any, blocking activity. These studies suggested that the smaller substitution at the 5 position, e.g., the proprionates and phenyl acyl, were more effective blockers of the efflux system than were those with larger substitutions. Derivatives bearing a substitution at C13 and C5 were also effective (e.g., 13-cyclopentyl-thio-5-proprionate tetracycline, IC$_{50}$=3.3 µM). Some of the drugs from this assay were then tested for their activity against the whole bacterial cells (See Experimental Series 4).

TABLE E4

5-Esters

| Cmpd | R | R$_1$ | IC$_{50}$ (µM)$^a$ |
|---|---|---|---|
| 1 | CH$_3$, H | COCH$_2$CH$_3$ | 1.0 |
| 2 | =CH$_2$ | COCH$_2$CH$_3$ | 0.2 |
| 3 | CH$_3$, H | COCH$_2$C$_6$H$_5$ | 1.6 |
| 4 | CH$_3$, H | CO(CH$_2$)$_6$CH$_3$ | 9.3 |

TABLE E4-continued

5-Esters

| Cmpd | R | R$_1$ | IC$_{50}$ (µM)$^a$ |
|---|---|---|---|
| 5 | —CH$_2$S-cyclopentyl, H | COCH$_2$CH$_3$ | 3.3 |
| 6 | CH$_3$, H | COCH$_2$CH$_2$CO$_2$H | 2.0 |
| 7 | CH$_3$, H | CO(CH$_2$)$_3$NH$_2$ | 6.4 |
| 8 | —CH$_2$S-propyl | COCH$_2$CH$_3$ | 1.4 |
| 9 | —CH$_2$S-cyclopentyl, H | cyclohexanoate | NE* |
| 10 | —CH$_2$S-cyclopentyl, H | cyclopentanoate | NE* |
| 11 | =CH$_2$ | cyclopropanoate | 9.4 |

$^a$by everted vessicle assay
*NE = no effect (>30 µM)

EXPERIMENTAL SERIES 4

The growth inhibitory effect of different C5 derivatives of tetracyclines, with and without doxycycline, were determined using sensitive and resistant *E. coli, Staphylococcus aureus,* and *Enterococcus faecalis.* The general protocol for these experiments was as follows:

Cultures were grown up fresh in L broth in the morning from an overnight culture. After 4–6 hours of growth, each bacterial culture was diluted to approximately 5×10$^5$ cells/ml. The drugs were diluted in two-fold dilutions from 50 µg/ml to <1 µg/ml and tested alone and in mixtures by incubation for 18 h at 37° C. The MIC was that concentration of drug alone or combination of drugs in which no growth (no cloudiness) was observed. The minimal lethal concentration (MLC) was that concentration which killed 99.9% of the cells and was based on the number of bacteria initially inoculated into the assays. Those cultures showing no bacterial growth after incubation at 37° C. were evaluated for the number of viable bacteria remaining by plating onto nutrient agar plates; these data determined the MLC. The results of four prototype drugs, the C5 propyl ester of methacycline, the C5 propyl ester of doxycycline and the combination of C5 propyl, C13 derivatives (13-cyclopentylthio-5-proprionate tetracycline and 13-propyl-thio-5-proprionate tetracycline) are presented in Table E5 and Charts 6–9.

TABLE E5

Susceptiblity of Tetracycline Susceptible Strains (MIC, µg/ml)

| C5 Ester | E. coli ML308 | S. aureus 450 | E. faecalis ATCC 9790 |
|---|---|---|---|
| 5 proprionate methacycline | 10 | 1.3 | .8 |
| 5 proprionate doxycycline | 10 | .6 | .4 |
| 13-cyclopentyl-thio-5-proprionate tetracycline | 20 | .4 | .4 |
| 13-propyl-thio-5-proprionate tetracycline | 20 | .3 | 2.5 |

Summary of Charts 6–9

Chart 6 MIC/MLC (µg/ml) dosages for tetracycline resistant strains using 5 proprionate methacycline with and without doxycycline.

Chart 7 MIC/MLC (μg/ml) dosages for tetracycline resistant strains using 5 proprionate doxycycline with and without doxycycline.

Chart 8 MIC/MLC (μg/ml) dosages for tetracycline resistant strains using 13-cyclopentyl-thio-5-proprionate tetracycline with and without doxycycline.

Chart 9 MIC/MLC (μg/ml) dosages for tetracycline resistant strains using 13-propyl-thio-5-proprionate tetracycline with and without doxycycline.

+=growth

0=no growth (MIC)

↓=killing

■=99.9% killing (MLC)

□=no growth, but no microbiologic testing

The analog concentration is given in columns A and H. It is this concentration which is within the squares 2–10. The deoxycycline concentration in the control is in Column 11 and its concentration in each of the boxes is given as small numbers within each of the squares.

CHART 6 A, B

Analog 5-proprionate methacycline Strain *E. coli* D1-299 (Tet A)

| A | 1 | 2 | 3 | 4 | 5 | 6 | 7 | 8 | 9 | 10 | 11 |
|---|---|---|---|---|---|---|---|---|---|---|---|
|   |   | \multicolumn{9}{c}{Analog} |   |
| A | Doxy | 50 | 25 | 12.5 | 6.25 | 3.12 | 1.56 | .78 | .39 | .195 | Doxy Control |
| B | 50 | 25.0 ■ | 37.5 | 43.8 | 46.7 | 48.4 | 49.2 | 49.6 | 49.8 | 49.9 | 50.0 ■ |
| C | 25 | 12.5 | 18.8 | 21.9 | 23.4 | 24.2 | 24.6 | 24.8 | 24.9 | 25.0 | 25.0 O |
| D | 12.5 | 6.25 | 9.4 | 11.0 | 11.7 O | 12.1 O | 12.3 + | 12.4 + | 12.5 + | 12.5 + | 12.5 + |
| E | 6.25 | 3.12 | 4.7 O | 5.5 + | 5.9 + | 6.1 + | 6.2 + | 6.23 + | 6.25 + | 6.25 + | 6.25 + |
| F | 3.12 | 1.56 ■ | 2.4 ■ | 2.8 + | 3.0 + | 3.05 + | 3.1 + | 3.12 + | 3.12 + | 3.12 + | 3.12 + |
| G | 1.56 | .78 ■ | 1.2 + | 1.4 + | 1.5 + | 1.53 + | 1.55 + | 1.56 + | 1.56 + | 1.56 + | 1.56 + |
| H | Analog Control | 50.00 ■ | 25.0 + | 12.5 + | 6.25 + | 3.12 + | 1.56 + | .78 + | .39 + | .195 + | 0.0 + |

Analog 5-proprionate methacycline Strain *S. aureus* 4250 (Tet K)

| B | 1 | 2 | 3 | 4 | 5 | 6 | 7 | 8 | 9 | 10 | 11 |
|---|---|---|---|---|---|---|---|---|---|---|---|
|   |   | \multicolumn{9}{c}{Analog} |   |
| A | Doxy | 50 | 25 | 12.5 | 6.25 | 3.12 | 1.56 | .78 | .39 | .195 | Doxy Control |
| B | 50 | 25.0 | 37.5 | 43.8 | 46.7 | 48.4 | 49.2 | 49.6 | 49.8 | 49.9 | 50.0 ■ |
| C | 25 | 12.5 | 18.8 | 21.9 | 23.4 | 24.2 | 24.6 | 24.8 | 24.9 | 25.0 | 25.0 ■ |
| D | 12.5 | 6.25 | 9.4 | 11.0 | 11.7 | 12.1 | 12.3 | 12.4 | 12.5 ↓ | 12.5 ↓ | 12.5 + |
| E | 6.25 | 3.12 | 4.7 | 5.5 | 5.9 | 6.1 | 6.2 ■ | 6.23 O | 6.25 + | 6.25 + | 6.25 + |
| F | 3.12 | 1.56 | 2.4 | 2.8 | 3.0 ■ | 3.05 ■ | 3.1 ↓ | 3.12 + | 3.12 + | 3.12 + | 3.12 + |
| G | 1.56 | .78 | 1.2 | 1.4 | 1.5 ■ | 1.53 ■ | 1.55 O | 1.56 + | 1.56 + | 1.56 + | 1.56 + |
| H | Analog Control | 50.00 | 25.0 | 12.5 | 6.25 ■ | 3.12 ■ | 1.56 + | .78 + | .39 + | .195 + | 0.0 + |

CHART 6 C, D

Analog 5-proprionate methacycline Strain *E. faecalis* 158 (Tet L)

| C | 1 | 2 | 3 | 4 | 5 | 6 | 7 | 8 | 9 | 10 | 11 |
|---|---|---|---|---|---|---|---|---|---|---|---|
|   |   | \multicolumn{9}{c}{Analog} |   |
| A | Doxy | 50 | 25 | 12.5 | 6.25 | 3.12 | 1.56 | .78 | .39 | .195 | Doxy Control |
| B | 50 | 25.0 | 37.5 | 43.8 | 46.7 | 48.4 | 49.2 | 49.6 | 49.8 | 49.9 | 50.0 |
| C | 25 | 12.5 | 18.8 | 21.9 | 23.4 | 24.2 | 24.5 | 24.8 | 24.9 | 25.0 | 25.0 ■ |
| D | 12.5 | 6.25 | 9.4 | 11.0 | 11.7 | 12.1 | 12.3 | 12.4 | 12.5 | 12.5 | 12.5 ■ |
| E | 6.25 | 3.12 | 4.7 | 5.5 | 5.9 | 6.1 | 6.2 | 6.23 | 6.25 O | 6.25 O | 6.25 + |
| F | 3.12 | 1.56 | 2.4 | 2.8 | 3.0 | 3.05 | 3.1 | 3.12 | 3.12 | 3.12 | 3.12 |

-continued

| | | | | | | | | | | | |
|---|---|---|---|---|---|---|---|---|---|---|---|
| G | 1.56 | .78 | 1.2 | 1.4 | 1.5 | 1.53 ■ | 1.55 ↓ | ○ 1.56 ○ + | ○ 1.56 + | + 1.56 + | + 1.56 + |
| H | Analog Control | 50.00 | 25.0 | 12.5 | 6.25 | 3.12 ■ | 1.56 ○ | .78 + | .39 + | .195 + | 0.0 + |

Analog 5-proprionate methacycline Strain E. faecalis 211 (Tet M)

| D | 1 | 2 | 3 | 4 | 5 | 6 | 7 | 8 | 9 | 10 | 11 |
|---|---|---|---|---|---|---|---|---|---|---|---|
| | | | | | | Analog | | | | | |
| A | Doxy | 50 | 25 | 12.5 | 6.25 | 3.12 | 1.56 | .78 | .39 | .195 | Doxy Control |
| B | 50 | 25.0 | 37.5 | 43.8 | 46.7 | 48.4 | 49.2 | 49.6 | 49.8 | 49.9 | 50.0 ■ |
| C | 25 | 12.5 | 18.8 | 21.9 | 23.4 | 24.2 | 24.6 | 24.8 | 24.9 | 25.0 | 25.0 ↓ |
| D | 12.5 | 6.25 | 9.4 | 11.0 | 11.7 | 12.1 ■ | 12.3 ○ | 12.4 + | 12.5 + | 12.5 + | 12.5 + |
| E | 6.25 | 3.12 | 4.7 | 5.5 ■ | 5.9 ■ | 6.1 + | 6.2 + | 6.23 + | 6.25 + | 6.25 + | 6.25 + |
| F | 3.12 | 1.56 | 2.4 | 2.8 ■ | 3.0 ↓ | 3.05 + | 3.1 + | 3.12 + | 3.12 + | 3.12 + | 3.12 + |
| G | 1.56 | .78 ■ | 1.2 ■ | 1.4 + | 1.5 + | 1.53 + | 1.55 + | 1.56 + | 1.56 + | 1.56 + | 1.56 + |
| H | Analog Control | 50.00 ■ | 25.0 ■ | 12.5 + | 6.25 + | 3.12 + | 1.56 + | .78 + | .39 + | .195 + | 0.0 + |

CHART 7 A, B

Analog 5-proprionate doxycycline Strain E. coli D1-299 (Tet A)

| A | 1 | 2 | 3 | 4 | 5 | 6 | 7 | 8 | 9 | 10 | 11 |
|---|---|---|---|---|---|---|---|---|---|---|---|
| | | | | | | Analog | | | | | |
| A | Doxy | 50 | 25 | 12.5 | 6.25 | 3.12 | 1.56 | .78 | .39 | .195 | Doxy Control |
| B | 50 | 25.0 | 37.5 | 43.8 | 46.7 | 48.4 | 49.2 | 49.6 | 49.8 | 49.9 | 50.0 ■ |
| C | 25 | 12.5 | 18.8 | 21.9 | 23.4 | 24.2 | 24.6 ○ | 24.8 ○ | 24.9 ○ | 25.0 + | 25.0 + |
| D | 12.5 | 6.25 | 9.4 ■ | 11.0 ○ | 11.7 + | 12.1 + | 12.3 + | 12.4 + | 12.5 + | 12.5 + | 12.5 + |
| E | 6.25 | 3.12 | 4.7 ■ | 5.5 + | 5.9 + | 6.1 + | 6.2 + | 6.23 + | 6.25 + | 6.25 + | 6.25 + |
| F | 3.12 | 1.56 ■ | 2.4 + | 2.8 + | 3.0 + | 3.05 + | 3.1 + | 3.12 + | 3.12 + | 3.12 + | 3.12 + |
| G | 1.56 ○ | .78 + | 1.2 + | 1.4 + | 1.5 + | 1.53 + | 1.55 + | 1.56 + | 1.56 + | 1.56 + | 1.56 + |
| H | Analog Control ↓ | 50.00 + | 25.0 + | 12.5 + | 6.25 + | 3.12 + | 1.56 + | .78 + | .39 + | .195 + | 0.0 + |

Analog 5-proprionate doxycycline Strain S. aureus 4250 (Tet K)

| B | 1 | 2 | 3 | 4 | 5 | 6 | 7 | 8 | 9 | 10 | 11 |
|---|---|---|---|---|---|---|---|---|---|---|---|
| | | | | | | Analog | | | | | |
| A | Doxy | 50 | 25 | 12.5 | 6.25 | 3.12 | 1.56 | .78 | .39 | .195 | Doxy Control |
| B | 50 | 25.0 | 37.5 | 43.8 | 46.7 | 48.4 | 49.2 | 49.6 | 49.8 | 49.9 | 50.0 |
| C | 25 | 12.5 | 18.8 | 21.9 | 23.4 | 24.2 | 24.6 | 24.8 | 24.9 | 25.0 | 25.0 ■ |
| D | 12.5 | 6.25 | 9.4 | 11.0 | 11.7 | 12.1 | 12.3 | 12.4 | 12.5 | 12.5 | 12.5 ○ |
| E | 6.25 | 3.12 | 4.7 | 5.5 | 5.9 | 6.1 | 6.2 | 6.23 ■ | 6.25 ↓ | 6.25 ○ | 6.25 + |
| F | 3.12 | 1.56 | 2.4 | 2.8 | 3.0 | 3.05 | 3.1 ■ | 3.12 ■ | 3.12 ○ | 3.12 + | 3.12 + |
| G | 1.56 | .78 | 1.2 | 1.4 | 1.5 | 1.53 ■ | 1.55 ■ | 1.56 ■ | 1.56 + | 1.56 + | 1.56 + |
| H | Analog | 50.00 | 25.0 | 12.5 | 6.25 | 3.12 ■ | 1.56 ↓ | .78 + | .39 + | .195 + | 0.0 + |

CHART 7 C, D

Analog 5-proprionate doxycycline Strain E. faecalis 158 (Tet L)

| C | 1 | 2 | 3 | 4 | 5 | 6 | 7 | 8 | 9 | 10 | 11 |
|---|---|---|---|---|---|---|---|---|---|----|----|
|   |   |   |   |   |   | Analog |   |   |   |    |    |
| A | Doxy | 50 | 25 | 12.5 | 6.25 | 3.12 | 1.56 | .78 | .39 | .195 | Doxy Control |
| B | 50 | 25.0 | 37.5 | 43.8 | 46.7 | 48.4 | 49.2 | 49.6 | 49.8 | 49.9 | 50.0 |
| C | 25 | 12.5 | 18.8 | 21.9 | 23.4 | 24.2 | 24.6 | 24.8 | 24.9 | 25.0 | 25.0 ■ |
| D | 12.5 | 6.25 | 9.4 | 11.0 | 11.7 | 12.1 | 12.3 | 12.4 | 12.5 | 12.5 | 12.5 ■ |
| E | 6.25 | 3.12 | 4.7 | 5.5 | 5.9 | 6.1 | 6.2 | 6.23 ■ | 6.25 ■ | 6.25 ■ | 6.25 + |
| F | 3.12 | 1.56 | 2.4 | 2.8 | 3.0 | 3.05 | 3.1 ■ | 3.12 ■ | 3.12 ■ | 3.12 + | 3.12 + |
| G | 1.56 | .78 | 1.2 | 1.4 | 1.5 | 1.53 | 1.55 ■ | 1.56 ■ | 1.56 ■ | 1.56 + | 1.56 + |
| H | Analog Control | 50.00 | 25.0 | 12.5 | 6.25 | 3.12 | 1.56 ■ | .78 ○ | .39 + | .195 + | 0.0 + |

Analog 5-proprionate doxycycline Strain E. faecalis 211 (Tet M)

| D | 1 | 2 | 3 | 4 | 5 | 6 | 7 | 8 | 9 | 10 | 11 |
|---|---|---|---|---|---|---|---|---|---|----|----|
|   |   |   |   |   |   | Analog |   |   |   |    |    |
| A | Doxy | 50 | 25 | 12.5 | 6.25 | 3.12 | 1.56 | .78 | .39 | .195 | Doxy Control |
| B | 50 | 25.0 | 37.5 | 43.8 | 46.7 | 48.4 | 49.2 | 49.6 | 49.8 | 49.9 | 50.0 ■ |
| C | 25 | 12.5 | 18.8 | 21.9 | 23.4 | 24.2 | 24.6 | 24.8 | 24.9 | 25.0 | 25.0 ■ |
| D | 12.5 | 6.25 | 9.4 | 11.0 | 11.7 | 12.1 ■ | 12.3 ■ | 12.4 ○ | 12.5 + | 12.5 + | 12.5 + |
| E | 6.25 | 3.12 | 4.7 | 5.5 | 5.9 ■ | 6.1 ↓ | 6.2 ○ | 6.23 + | 6.25 + | 6.25 + | 6.25 + |
| F | 3.12 | 1.56 | 2.4 ■ | 2.8 ■ | 3.0 ○ | 3.05 + | 3.1 + | 3.12 + | 3.12 + | 3.12 + | 3.12 |
| G | 1.56 | .78 | 1.2 | 1.4 ■ | 1.5 ■ | 1.53 ○ | 1.55 + | 1.56 + | 1.56 + | 1.56 + | 1.56 + |
| H | Analog Control | 50.00 | 25.0 | 12.5 | 6.25 ■ | 3.12 ○ | 1.56 + | .78 + | .39 + | .195 + | 0.0 + |

CHART 8 A, B

Analog 13-cyclopentyl-thio-5-proprionate tetracycline Strain E. coli D1-299 (Tet A)

| A | 1 | 2 | 3 | 4 | 5 | 6 | 7 | 8 | 9 | 10 | 11 |
|---|---|---|---|---|---|---|---|---|---|----|----|
|   |   |   |   |   |   | Analog |   |   |   |    |    |
| A | Doxy | 50 | 25 | 12.5 | 6.25 | 3.12 | 1.56 | .78 | .39 | .195 | Doxy Control |
| B | 50 | 25.0 | 37.5 | 43.8 | 46.7 | 48.4 | 49.2 | 49.6 | 49.8 | 49.9 | 50.0 ■ |
| C | 25 | 12.5 | 18.8 | 21.9 | 23.4 | 24.2 | 24.6 | 24.8 ■ | 24.9 ↓ | 25.0 + | 25.0 + |
| D | 12.5 | 6.25 | 9.4 | 11.0 | 11.7 | 12.1 | 12.3 ■ | 12.4 ○ | 12.5 + | 12.5 + | 12.5 + |
| E | 6.25 | 3.12 | 4.7 | 5.5 | 5.9 ■ | 6.1 + | 6.23 + | 6.23 + | 6.25 + | 6.25 + | 6.25 + |
| F | 3.12 | 1.56 + | 2.4 + | 2.8 + | 3.0 + | 3.05 + | 3.1 + | 3.12 + | 3.12 + | 3.12 + | 3.12 + |
| G | 1.56 | .78 + | 1.2 + | 1.4 + | 1.5 + | 1.53 + | 1.55 + | 1.56 + | 1.56 + | 1.56 + | 1.56 + |
| H | Analog Control | 50.00 + | 25.0 + | 12.5 + | 6.25 + | 3.12 + | 1.56 + | .78 + | .39 + | .195 + | 0.0 + |

-continued

Analog 13-cyclopentyl-thio-5-proprionate tetracycline Strain *S. aureus* 4250 (Tet K)

| B | 1 | 2 | 3 | 4 | 5 | 6 | 7 | 8 | 9 | 10 | 11 |
|---|---|---|---|---|---|---|---|---|---|---|---|
| | | | | | | Analog | | | | | |
| A | Doxy | 50 | 25 | 12.5 | 6.25 | 3.12 | 1.56 | .78 | .39 | .195 | Doxy Control |
| B | 50 | 25.0 | 37.5 | 43.8 | 46.7 | 48.4 | 49.1 | 49.6 | 49.8 | 49.9 | 50.0 |
| C | 25 | 12.5 | 18.8 | 21.9 | 23.4 | 24.2 | 24.6 | 24.8 | 24.9 | 25.0 | 25.0 ■ |
| D | 12.5 | 6.25 | 9.4 | 11.0 | 11.7 | 12.1 | 12.3 | 12.4 | 12.5 | 12.5 | 12.5 ○ |
| E | 6.25 | 3.12 | 4.7 | 5.5 | 5.9 | 6.1 | 6.2 | 6.23 | 6.25 ■ | 6.25 ■ | 6.25 + |
| F | 3.12 | 1.56 | 2.4 | 2.8 | 3.0 | 3.05 | 3.1 | 3.12 | 3.12 ■ | 3.12 ■ | 3.12 + |
| G | 1.56 | .78 | 1.2 | 1.4 | 1.5 | 1.53 | 1.55 | 1.56 | 1.56 ■ | 1.56 ■ | 1.56 + |
| H | Analog Control | 50.00 | 25.0 | 12.5 | 6.25 | 3.12 | 1.56 | .78 | .39 ■ | .195 ■ | 0.0 + |

CHART 8 C, D

Analog 13-cyclopentyl-thio-5-proprionate tetracycline Strain *E. faecalis* 158 (Tet L)

| C | 1 | 2 | 3 | 4 | 5 | 6 | 7 | 8 | 9 | 10 | 11 |
|---|---|---|---|---|---|---|---|---|---|---|---|
| | | | | | | Analog | | | | | |
| A | Doxy | 50 | 25 | 12.5 | 6.25 | 3.12 | 1.56 | .78 | .39 | .195 | Doxy Control |
| B | 50 | 25.0 | 37.5 | 43.8 | 46.7 | 48.4 | 49.2 | 49.6 | 49.8 | 49.9 | 50.0 |
| C | 25 | 12.5 | 18.8 | 21.9 | 23.4 | 24.2 | 24.6 | 24.8 | 24.9 | 25.0 | 25.0 ■ |
| D | 12.5 | 6.25 | 9.4 | 11.0 | 11.7 | 12.1 | 12.3 | 12.4 | 12.5 | 12.5 | 12.5 ■ |
| E | 6.25 | 3.12 | 4.7 | 5.5 | 5.9 | 6.1 | 6.2 | 6.23 | 6.25 ■ | 6.25 ■ | 6.25 + |
| F | 3.12 | 1.56 | 2.4 | 2.8 | 3.0 | 3.05 | 3.1 | 3.12 | 3.12 ■ | 3.12 ■ | 3.12 + |
| G | 1.56 | .78 | 1.2 | 1.4 | 1.5 | 1.53 | 1.55 | 1.56 | 1.56 ■ | 1.56 ■ | 1.56 + |
| H | Analog Control | 50.00 | 25.0 | 12.5 | 6.25 | 3.12 | 1.56 | .78 | .39 ■ | .195 ■ | 0.0 + |

Analog 13-cyclopentyl-thio-5-proprionate tetracycline Strain *E. faecalis* 211 (Tet M)

| D | 1 | 2 | 3 | 4 | 5 | 6 | 7 | 8 | 9 | 10 | 11 |
|---|---|---|---|---|---|---|---|---|---|---|---|
| | | | | | | Analog | | | | | |
| A | Doxy | 50 | 25 | 12.5 | 6.25 | 3.12 | 1.56 | .78 | .39 | .195 | Doxy Control |
| B | 50 | 25.0 | 37.5 | 43.8 | 46.7 | 48.4 | 49.2 | 49.6 | 49.8 | 49.9 | 50.0 |
| C | 25 | 12.5 | 18.8 | 21.9 | 23.4 | 24.2 | 24.6 | 24.8 | 24.9 | 25.0 | 25.0 ■ |
| D | 12.5 | 6.25 | 9.4 | 11.0 | 11.7 | 12.1 | 12.3 | 12.4 | 12.5 ■ | 12.5 ■ | 12.5 + |
| E | 6.25 | 3.12 | 4.7 | 5.5 | 5.9 | 6.1 | 6.2 | 6.23 ■ | 6.25 ■ | 6.25 + | 6.25 + |
| F | 3.12 | 1.56 | 2.4 | 2.8 | 3.0 | 3.05 | 3.1 | 3.12 | 3.12 ○ | 3.12 + | 3.12 + |
| G | 1.56 | .78 | 1.2 | 1.4 | 1.5 | 1.53 | 1.55 | 1.56 | 1.56 ○ | 1.56 + | 1.56 + |
| H | Analog Control | 50.00 | 25.0 | 12.5 | 6.25 | 3.12 | 1.56 | .78 | .39 ○ | .195 + | 0.0 + |

CHART 9 A, B

Analog 13-propyl-thio-5-proprionate Strain *E. coli* D1-299 (Tet A)

| A | 1 | 2 | 3 | 4 | 5 | 6 | 7 | 8 | 9 | 10 | 11 |
|---|---|---|---|---|---|---|---|---|---|---|---|
| | | | | | | Analog | | | | | |
| A | Doxy | 50 | 25 | 12.5 | 6.25 | 3.12 | 1.56 | .78 | .39 | .195 | Doxy |

-continued

|   |   |   |   |   |   |   |   |   |   |   | Control |
|---|---|---|---|---|---|---|---|---|---|---|---|
| B | 50 | 25.0 | 37.5 | 43.8 | 46.7 | 48.4 | 49.2 | 49.6 | 49.8 | 49.9 | 50.0 |
| C | 25 | 12.5 | 18.8 | 21.9 | 23.4 | 24.2 | 24.6 | 24.8 | 24.9 | 25.0 | 25.0 ○ |
| D | 12.5 | 6.25 | 9.4 | 11.0 | 11.7 | 12.1 | 12.3 ○ | 12.4 + | 12.5 + | 12.5 + | 12.5 + |
| E | 6.25 | 3.12 + | 4.7 + | 5.5 + | 5.9 + | 6.1 + | 6.2 + | 6.23 + | 6.25 + | 6.25 + | 6.25 + |
| F | 3.12 | 1.56 + | 2.4 + | 2.8 + | 3.0 + | 3.05 + | 3.1 + | 3.12 + | 3.12 + | 3.12 + | 3.12 + |
| G | 1.56 | .78 + | 1.2 + | 1.4 + | 1.5 + | 1.53 + | 1.55 + | 1.56 + | 1.56 + | 1.56 + | 1.56 + |
| H | Analog Control | 50.00 + | 25.0 + | 12.5 + | 6.25 + | 3.12 + | 1.56 + | .78 + | .39 + | .195 + | 0.0 + |

Analog 13-propyl-thio-5-proprionate Strain *S. aureus* 4250 (Tet K)

| B | 1 | 2 | 3 | 4 | 5 | 6 | 7 | 8 | 9 | 10 | 11 |
|---|---|---|---|---|---|---|---|---|---|---|---|
|   |   |   |   |   |   | Analog |   |   |   |   |   |
| A | Doxy | 50 | 25 | 12.5 | 6.25 | 3.12 | 1.56 | .78 | .39 | .195 | Doxy Control |
| B | 50 | 25.0 | 37.5 | 43.8 | 46.7 | 48.4 | 49.2 | 49.6 | 49.8 | 49.9 | 50.0 |
| C | 25 | 12.5 | 18.8 | 21.9 | 23.4 | 24.2 | 24.6 | 24.8 | 24.9 | 25.0 | 25.0 ■ |
| D | 12.5 | 6.25 | 9.4 | 11.0 | 11.7 | 12.1 | 12.3 | 12.4 | 12.5 | 12.5 | 12.5 + |
| E | 6.25 | 3.12 | 4.7 | 5.5 | 5.9 | 6.1 | 6.2 | 6.23 | 6.25 | 6.25 | 6.25 + |
| F | 3.12 | 1.56 | 2.4 | 2.8 | 3.0 | 3.05 | 3.1 | 3.12 | 3.12 ■ | 3.12 ○ | 3.12 + |
| G | 1.56 | .78 | 1.2 | 1.4 | 1.5 | 1.53 | 1.55 | 1.56 | 1.56 ■ | 1.56 + | 1.56 + |
| H | Analog Control | 50.00 | 25.0 | 12.5 | 6.25 | 3.12 | 1.56 ■ | .78 ■ | .39 + | .195 + | 0.0 + |

CHART 9 C, D

Analog 13-propyl-thio-5-proprionate Strain *E. faecalis* 158 (Tet L)

| C | 1 | 2 | 3 | 4 | 5 | 6 | 7 | 8 | 9 | 10 | 11 |
|---|---|---|---|---|---|---|---|---|---|---|---|
|   |   |   |   |   |   | Analog |   |   |   |   |   |
| A | Doxy | 50 | 25 | 12.5 | 6.25 | 3.12 | 1.56 | .78 | .39 | .195 | Doxy Control |
| B | 50 | 25.0 | 37.5 | 43.8 | 46.7 | 48.4 | 49.2 | 49.6 | 49.8 | 49.9 | 50.0 |
| C | 25 | 12.5 | 18.8 | 21.9 | 23.4 | 24.2 | 24.6 | 24.8 | 24.9 | 25.0 | 25.0 |
| D | 12.5 | 6.25 | 9.4 | 11.0 | 11.7 | 12.1 | 12.3 | 12.4 | 12.5 | 12.5 | 12.5 ↓ |
| E | 6.25 | 3.12 | 4.7 | 5.5 | 5.9 | 6.1 | 6.2 | 6.23 | 6.25 | 6.25 | 6.25 + |
| F | 3.12 | 1.56 | 2.4 | 2.8 | 3.0 | 3.05 | 3.1 | 3.12 ■ | 3.12 ○ | 3.12 + | 3.12 + |
| G | 1.56 | .78 | 1.2 | 1.4 | 1.5 | 1.53 | 1.55 | 1.56 ■ | 1.56 ○ | 1.56 + | 1.56 + |
| H | Analog Control | 50.00 | 25.0 | 12.5 | 6.25 | 3.12 ■ | 1.56 ■ | .78 + | .39 + | .195 + | 0.0 + |

Analog 13-propyl-thio-5-proprionate Strain *E. faecalis* 211 (Tet M)

| D | 1 | 2 | 3 | 4 | 5 | 6 | 7 | 8 | 9 | 10 | 11 |
|---|---|---|---|---|---|---|---|---|---|---|---|
|   |   |   |   |   |   | Analog |   |   |   |   |   |
| A | Doxy | 50 | 25 | 12.5 | 6.25 | 3.12 | 1.56 | .78 | .39 | .195 | Doxy Control |
| B | 50 | 25.0 | 37.5 | 43.8 | 46.7 | 48.4 | 49.2 | 49.6 | 49.8 | 49.9 | 50.0 |
| C | 25 | 12.5 | 18.8 | 21.9 | 23.4 | 24.2 | 24.6 | 24.8 | 24.9 | 25.0 | 25.0 ↓ |
| D | 12.5 | 6.25 | 9.4 | 11.0 | 11.7 | 12.1 | 12.3 | 12.4 | 12.5 + | 12.5 + | 12.5 + |
| E | 6.25 | 3.12 | 4.7 | 5.5 | 5.9 | 6.1 | 6.2 + | 6.23 + | 6.25 + | 6.25 + | 6.25 + |
| F | 3.12 | 1.56 | 2.4 | 2.8 | 3.0 | 3.05 ○ | 3.1 + | 3.12 + | 3.12 + | 3.12 + | 3.12 + |
| G | 1.56 | .78 | 1.2 | 1.4 | 1.5 | 1.53 ○ | 1.55 + | 1.56 + | 1.56 + | 1.56 + | 1.56 + |

| | | | | | | | | | | |
|---|---|---|---|---|---|---|---|---|---|---|
| H | Analog Control | 50.00 | 25.0 | 12.5 | 6.25 ■ | 3.12 ○ | 1.56 + | .78 + | .39 + | .195 + | 0.0 + |

All four tetracycline derivatives effectively inhibit growth of sensitive *Staph aureus* and *E. faecalis* when used alone. None was effective alone against susceptible *E. coli* (Table E5). Against the tetracycline resistant *S. aureus* and *E. faecalis* strains, the analogs were also very effective alone (Charts 6–9). While they were not effective alone against resistant *E. coli* D1-299, they did show synergistic effects achieving both decreased growth and cell killing. For instance, at a combination of 5.9 µg/ml of doxycyline and 6.25 µg/ml of 13-cyclopentyl-thio-5-proprionate Tc, there was an MLC of *E. coli* D1-299 (Chart 8A). The 13-cyclopentyl-thio-5-proprionate tetracycline was equally effective alone against Tet K in *S. aureus* and Tet L and Tet M determinants in *E. faecalis*. In fact, the values of the MLC/MLC were close to those of the sensitive strains (Table E5).

The C5 proprionate esters were also effective alone against resistant *S. aureus* and *E. faecalis*, and showed further efficacy in additiveness and synergy when used with doxycycline in MIC and MLC. For instance, in Chart 6B, the combination of 1.55 µg/ml doxycycline and 1.56 µg/ml 5-proprionate methacycline or 6.23 µg/ml doxycycline and 0.78 µg/ml analog achieved MIC.

The growth inhibition included cells bearing different tetracycline efflux systems (Class A, B, K & L) and a ribosomal protection system (Class M). These unexpected results confirm that the substitution at the C5 position produces an effective efflux blocking agent which demonstrates synergistic antibacterial activity against tetracycline resistant bacteria bearing different resistance determinants.

EXAMPLE 1

Synthesis of 13-propylthio-5-hydroxy-6-α-deoxy-tetracycline

Methacycline hydrochloride (5.0 g, 10.4 mmol) was placed in a round-bottom flask and suspended in 100 mL of EtOH. Twenty mL of propanethiol (16.8 g, 0.270 mol) and AIBN 250 mg, were added and the reaction mixture refluxed with stirring for 12 h while under $N_2$. The mixture was reduced to ⅕ volume by distillation and filtered. The filtrate was dripped slowly into cold $Et_2O$ while stirring resulting in the formation of a yellow precipitate. The precipitate was filtered, dissolved in $H_2O$ and brought to pH 4.5 with 1.0M NaOH. This solution was filtered, and extracted with $CH_2Cl_2$ yielding a dark yellow solid (620 mg). The solid was dissolved in MeOH and treated with charcoal yielding a yellow solid in low yield (25%, 256 mg) mp=130°–140° C. (dec.). TLC $r_f$=0.70 (I); HPLC $R_t$=20.18 min. HNMR (DMSO-$d_6$)δ 7.50 (t, 1 H), 7.05 (d, 1 H), 6.85 (d, 1 H), 4.32 (d, 2 H), 3.15 (s, 1 H), 2.65 (s, 6 H), 2.32–2.52 (m, 2 H), 1.51–1.80 (m, 2 H), 0.9–1.22 (m, 3 H); HRMS (FAB); calc for $C_{25}H_{30}N_2O_8S$ 519.1801 (M+1), found 519.1815 (M+1).

EXAMPLE 2

Synthesis of 13-cyclopentylthio-5-hydroxy-6-α-deoxy-tetracycline

This compound was prepared substantially as described in Example 1. Purification was either by column chromatography on EDTA silica, extraction pH 4.5 into $CH_2Cl_2$, or by HPLC chromatography. An analytical sample was produced by HPLC as a yellow solid of mp=132°–139° C. (dec.) in moderate yield (28.3%). Higher yields were obtained by the extraction method and treatment with activated charcoal in MeOH (32.1%); TLC $r_f$=0.80 (I); HPLC $R_t$=21.19 min. HNMR (MeOH-$d_4$)δ 7.38 (t, 1H), 7.02 (d, 1H), 6.72 (d, 1H), 4.10 (s, 2 H), 2.70 (br s, 6 H), 1.81–2.01 (br m, 2 H), 1.28–1.75 (br m, 6 H), (br m, 2 H); HRMS (FAB); calc for $C_{27}H_{32}N_2O_8S$ 545.1957 (M+1), found 545.1960 (M+1).

EXAMPLE 3

Synthesis of 13-propylthio-5-proprionate-6-deoxy-tetracycline 100 mg of 13-propylthio-5-hydroxy-6-α-deoxy-tetracycline of Example 1 and 2.0 g of propionic acid were dissolved in 20 mL of anhydrous hydrofluoric acid and the resultant solution sealed in a polypropylene tube for 3 days at room temperature. The hydrofluoric acid was removed by a slow steady stream of nitrogen and the residue taken up in diethyl ether. The precipitate was dissolved in MeOH (4 mL) and injected into a preparative HPLC utilizing a C18 reverse-phase column and mobile phases of phosphate buffer (pH 4.5) and MeOH over a linear gradient (30%–100% over 30 minutes) at 30 mL/minute. The compound was collected at 26.7–29.3 minutes, extracted into 40 mL n-butanol, and the solvent removed in vacuo to yield 34 mg of pure product. MS data=M+1 (FAB) 575, 558, 541, 484.

EXAMPLE 4

Synthesis of 13-cyclopentylthio-5-proprionate-6-deoxy tetracycline 100 mg of 13-cyclopentylthio-5-hydroxy-6-α-deoxytetracycline of Example 2 and 5.0 g of propionic acid were dissolved in 35 mL of anhydrous hydrofluoric acid and the resultant solution sealed in a polypropylene tube for 3 days at room temperature. The hydrofluoric acid was removed by a slow steady stream of nitrogen and the residue taken up in diethyl ether. The precipitate was dissolved in MeOH (4 mL) and injected into a preparative HPLC utilizing a C18 reverse-phase column and mobile phases of phosphate buffer (pH 4.5) and MeOH over a linear gradient (30%–100% over 30 minutes) at 30 mL/minute. The compound was collected at 26.7–29.3 minutes, extracted into 40 mL n-butanol, and the solvent removed in vacuo to yield 34 mg of pure product. MS data=M+1 (FAB) 601, 492, 391.

The present invention is not to be restricted in form nor limited in scope except by the claims appended hereto.

I claim:

1. A pharmaceutical composition for converting tetracycline resistant bacteria into tetracycline sensitive bacteria comprising a C5 ester of tetracycline and a tetracycline-type antibiotic which is not a C5 ester of tetracycline, and a pharmaceutically acceptable carrier.

2. A pharmaceutical composition for converting tetracycline resistant bacteria into tetracycline sensitive bacteria comprising a 13,5 derivative of tetracycline and a tetracycline-type antibiotic which is not a 13,5 derivative of tetracycline, and a pharmaceutically acceptable carrier.

3. A pharmaceutical composition according to claim 2 wherein the tetracycline-type antibiotic is a tetracycline, a tetracycline analogue or a tetracycline derivative.

4. A pharmaceutical composition according to claim 2 wherein the tetracycline-type antibiotic is selected from inocycline, doxyxyxline, methacycline, demeclocycline, oxytetracycline, or chlortetracycline.

5. C5 esters having the formula

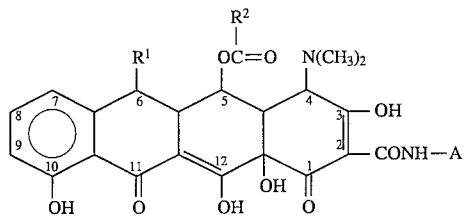

wherein $R_1$ and $R_2$ are selected from the group consisting of a methylene group, hydroxyl, hydrogen or a group consisting of organic entities comprising from 1–12 carbon atoms, with or without other heteroatoms including sulfur, oxygen, halogen, nitrogen, and the like, and takes form as linear, branched, or cyclic alkyl, aryl, or alkylaryl structures; and A is selected from the group consisting of a methylene groups, and any linear, branched, or ling structure comprising from 1–6 carbon atoms and optionally including heteroatoms of oxygen and nitrogen.

6. A composition of claim 5, wherein $R_1$ is $CH_3$ and $R_2$ is $CH_2CH_3$; $R_1$ is $=CH_2$ and $R_2$ is $CH_2CH_3$; $R_1$ is $-CH_2-$S-cyclopentyl and $R_2$ is $CH_2CH_3$; or $R_1$ is $-CH_2-$S-propyl and $R_2$ is $CH_2CH_3$.

7. A pharmaceutical preparation according to claim 1 wherein the tetracycline-type antibiotic is a tetracycline, a tetracycline analogue or a tetracycline derivative.

8. A pharmaceutical preparation according to claim 1 wherein the tetracycline-type antibiotic is selected from minocycline, doxycycline, methacycline, demecycline, oxytetracycline, or chlortetracycline.

9. A compound of the following formula

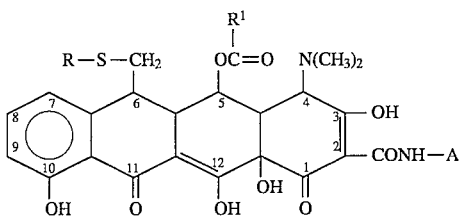

where R is an organic entity comprising 1–12 carbon atoms and optionally including one or more heteroatoms or halogen atoms;

$R^1$ is an organic entity comprising 1–12 carbon atoms and optionally including one or more heteroatoms or halogen atoms; and A is a hydrogen atom, a methylene group and any linear, branched or ring structure comprising from 1–6 carbon atoms and optionally including one or more heteroatoms.

10. A compound of claim 9 where 1) R is cyclopentyl, $R^1$ is $CH_2CH_3$ and A is H; 2) R is propyl, $R^1$ is $CH_2CH_3$ and A is H; 3) R is cyclopentyl, $R^1$ is cyclohexyl and A is H; or 4) R is cyclopentyl, $R^1$ is cyclopentyl and A is H.

11. A method for converting tetracycline resistant bacteria into tetracycline sensitive bacteria, comprising contacting the resistant bacteria with a predetermined quantity of at least a first composition selected from C5 esters of tetracycline or a 13,5 derivative of tetracycline, and concomitantly administering to the cell a predetermined quantity of at least a second composition selected from a tetracycline, a tetracycline analogue or a tetracycline derivative which is not a C5 ester of tetracycline nor a 13,5 derivative of tetracycline.

12. The method of claim 11 wherein a subinhibitory amount of the first composition is administered to the cell.

13. A method according to claim 11 wherein said first composition is a C5 ester.

14. A method according to claim 11 wherein said first composition is a 13,5 derivative.

15. A method according to claim 11 wherein said second composition is tetracycline.

16. A method according to claim 11 wherein said second composition is minocycline, doxycycline, methacycline, demeclocycline, oxytetracycline, or chlortetracycline.

17. A method for exerting cidal activity against susceptible bacteria, comprising:

administering to the susceptible bacteria a predetermined quantity of a first composition of the following formula:

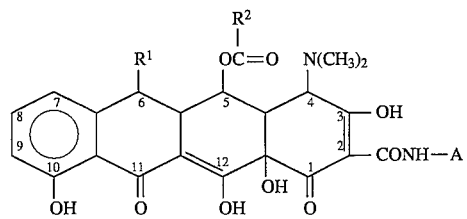

where $R_1$ and $R_2$ are each independently selected from the group consisting of a methylene group, hydroxyl, hydrogen or an organic entity comprising 1–12 carbon atoms optionally including one or more heteroatoms or halogen atoms; and A is a hydrogen atom, a methylene group and any linear, branched or ring structure comprising from 1–6 carbon atoms and optionally including one or more heteroatoms; and optionally, concomitantly administering to the bacteria a predetermined quantity of at least a second composition selected from the chemical group consisting of tetracycline, tetracycline analogues, and tetracycline derivatives which are the first composition.

18. The method of claim 17 wherein the predetermined quantity of the second composition is concomitantly administered to the bacteria.

19. The method of claim 17 wherein the second composition is not administered to the bacteria.

20. The method according to claim 17 where $R_1$ is $-CH_2S-$R with R being an organic entity having 1–12 carbon atoms and optionally including one or more heteroatoms or halogen atoms.

21. The method according to claim 17 where $R_1$ is $CH_3$ and $R_2$ is $CH_2CH_3$; $R_1$ is $=CH_2$ and $R_2$ is $CH_2CH_3$; $R_1$ is $-CH_2-$S-cyclopentyl and $R_2$ is $CH_2CH_3$; or $R_1$ is $-CH_2-$S-propyl and $R_2$ is $CH_2CH_3$.

22. The method according to claim 17 where 1) $R_1$ is $CH_3$, $R_2$ is $CH_2CH_3$ and A is H; 2) $R_1$ is $=CH_2$, $R_2$ is $CH_2CH_3$ and A is H; 3) $R_1$ is $CH_3$, $R_2$ is $CH_2C_6H_5$ and A is H; 4) $R_1$ is $CH_3$, $R_2$ is $(CH_2)_6CH_3$ and A is H; 5) $R_1$ is $CH_2S$-cyclopentyl, $R_2$ is $CH_2CH_3$ and A is H; 6) $R_1$ is $CH_3$, $R_2$ is $(CH_2)_2COOH$ and A is H; 7) $R_1$ is $CH_3$, $R_2$ is $(CH_2)_3NH_2$ and A is H; 8) $R_1$ is $CH_2S$-propyl, $R_2$ is $CH_2CH_3$ and A is H; 9) $R_1$ is $CH_2S$-cyclopentyl, $R_2$ is cyclohexyl and A is H;

10) $R_1$ is $CH_2S$-cyclopentyl, $R_2$ is cyclopentyl and A is H; or 11) $R_1$ is $=CH_2$, $R_2$ is cyclopropyl and A is H.

23. A method for therapeutically treating tetracycline sensitive or resistant bacteria, comprising:

administering to the bacteria a predetermined quantity of a compound of the following formula:

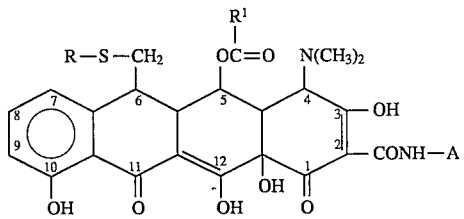

where R is an organic entity comprising 1–12 carbon atoms and optionally including one or more heteroatoms or halogen atoms;

$R^1$ is an organic entity comprising 1–12 carbon atoms and optionally including one or more heteroatoms or halogen atoms; and A is a hydrogen atom, a methylene group and any linear, branched or ring structure comprising from 1–6 carbon atoms and optionally including one or more heteroatoms.

24. The method of claim 23 wherein the bacteria is a gram positive bacteria.

25. The method of claim 23 wherein the bacteria is tetracycline resistant.

26. The method of claim 23 wherein the bacteria is *S. aureus* or *E. faecalis*.

27. The method according to claim 23 wherein 1) R is cyclopentyl, $R^1$ is $CH_2CH_3$ and A is H; 2) R is propyl, $R^1$ is $CH_2CH_3$ and A is H; 3) R is cyclopentyl, $R^1$ is cyclohexyl and A is H; or 4) R is cyclopentyl, $R^1$ is cyclopentyl and A is H.

* * * * *